United States Patent [19]

Derungs et al.

[11] Patent Number: 5,376,674
[45] Date of Patent: Dec. 27, 1994

[54] OXETANONE COMPOUNDS CONTAINING PROLINE AND PHARMACEUTICAL COMPOSITIONS THEREOF

[75] Inventors: Romano Derungs, Riehen; Hans P. Märki; Henri Stalder, both of Basel; André Szente, Riehen, all of, Switzerland

[73] Assignee: Hoffman-La Roche Inc., Nutley, N.J.

[21] Appl. No.: 77,490

[22] Filed: Jun. 14, 1993

Related U.S. Application Data

[60] Division of Ser. No. 928,907, Aug. 12, 1992, Pat. No. 5,260,310, which is a continuation of Ser. No. 653,847, Feb. 11, 1991, abandoned.

[30] Foreign Application Priority Data

Feb. 26, 1990 [CH] Switzerland .............. 604/90
Dec. 17, 1990 [CH] Switzerland .............. 4005/90

[51] Int. Cl.$^5$ .............. A61K 31/40; C07D 405/12
[52] U.S. Cl. .............. 514/422; 548/517
[58] Field of Search .............. 548/417; 514/422

[56] References Cited

U.S. PATENT DOCUMENTS 4,189,438 2/1980 Umezawa et al. .
4,202,824 5/1980 Umezawa et al. .
4,242,453 12/1980 Umezawa et al. .
4,931,463 6/1990 Barbier et al. .
4,983,746 1/1991 Barbier et al. .

FOREIGN PATENT DOCUMENTS

WO8810258 12/1988 WIPO .

OTHER PUBLICATIONS

DiMagno, et al. *New England Journal of Medicine*, 288:813–815 (1973).

*Primary Examiner*—Nicky Chan
*Attorney, Agent, or Firm*—George M. Gould; William H. Epstein; Catherine A. Picut

[57] ABSTRACT

Novel compounds of the formula

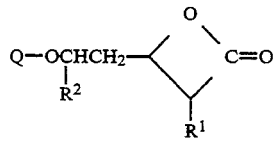

wherein Q, $R^1$ and $R^2$ are described herein, are disclosed along with pharmaceutical compositions, methods of use, and process for producing compounds of formula I which starts from the corresponding β-hydroxycarboxylic acids.

9 Claims, No Drawings

OXETANONE COMPOUNDS CONTAINING PROLINE AND PHARMACEUTICAL COMPOSITIONS THEREOF

RELATED APPLICATIONS

This patent application is a divisional application of patent application 07/928,907, filed Aug. 12, 1992, which issued as U.S. Pat. No. 5,260,310, which is a continuation of parent application 07/653,847, filed Feb. 11, 1991, now abandoned.

BACKGROUND OF THE INVENTION

1. Field of the Invention

The present invention is concerned with novel oxetanones, a process for their manufacture, pharmaceutical preparations which contain such oxetanones as well as the use of these oxetanones in the manufacture of pharmaceutical preparations.

2. Summary of the Invention

The present invention describes compounds having the formula

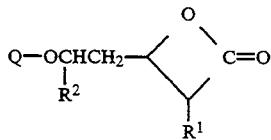

wherein Q is a group having the formula $(R^3,R^4)NCO(X)_n$—CO—  Q$^1$
$(R^3,R^4)NCO$—X′—  Q$^2$ or

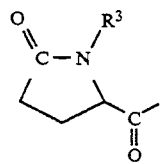  Q$^3$ and $R^1$ and $R^2$ each are independently alkyl with up to 18C atoms substituted by 1 to 3 halogen atoms or alkyl, alkenyl, alkynyl or alkadienyl groups with up to 20C atoms optionally interrupted by a 1,4-arylene group, optionally substituted by an aryl group in the ω-position and optionally substituted by an aryl-$C_{1-4}$-alkyl group, whereby $R^1$ can be interrupted by an O or S atom or by a sulphinyl or sulphonyl group in a position other than the a-position to an unsaturated C atom, or $R^1$ is an aryl—NH— or aryl—$C_{1-4}$—alkyl—OCONH— group, $R^3$ and $R^4$ each are independently hydrogen or $C_{1-4}$-alkyl or together with the N atom to which they are attached form a saturated 3- to 6-membered ring optionally containing an O or S atom in a position other than the a-position to the N atom, n is the number 1 or 0, X is an alkylene group which contains up to 6C atoms, which is optionally interrupted by an O or S atom or by a sulphinyl or sulphonyl group and which is optionally substituted by a hydroxy, mercapto, aryl, aryloxy, arylthio, aryl-$C_{1-4}$-alkyl, aryl-$C_{1-4}$-alkoxy, aryl-$C_{1-4}$-alkylthio, aryl-$C_{1-4}$-alkylidene, $C_{3-7}$-cycloalkylidene or $C_{1-6}$-alkylidene group or by one or two $C_{1-6}$-alkyl, $C_{1-6}$-alkoxy or $C_{1-6}$-alkylthio groups, whereby two $C_{1-6}$-alkyl, $C_{1-6}$-alkoxy or $C_{1-6}$-alkylthio groups on the same C atom or on two adjacent C atoms can form an optionally mono-unsaturated 3- to 7-membered ring and an optionally present hydroxy or mercapto group or an optionally present unsaturated C atom must be in a position other than the a-position to an optionally present O or S atom or to an optionally present sulphinyl or sulphonyl group, or X is a group of the formula =CHN(R,R$^o$) or —CHN(R,R$^o$)CH$_2$— where R and R$^o$ each are independently hydrogen $C_{1-4}$-alkyl, $C_{1-4}$-alkyl(CO or OCO)—, aryl, aryl(CO or OCO)—, aryl-$C_{1-4}$-alkyl or aryl-$C_{1-4}$-alkyl(CO or OCO)— and X′ is an alkylene group containing up to 6C atoms which can be substituted by a $C_{1-4}$-alkoxy, aryl, aryloxy, arylthio, aryl-$C_{1-4}$-alkyl, aryl-$C_{1-4}$-alkoxy or aryl-$C_{1-4}$-alkylthio group or by one or two $C_{1-6}$-alkyl groups, whereby two $C_{1-6}$-alkyl groups attached to adjacent C atoms can form a 3- to 7-membered ring.

DETAILED DESCRIPTION OF THE INVENTION

The present invention describes compounds having the formula

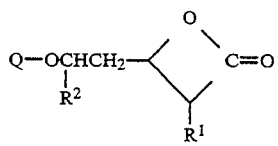  I wherein Q is a group having the formula $(R^3,R^4)NCO(X)_n$—CO—  Q$^1$
$(R^3,R^4)NCO$—X′—  Q$^2$ or

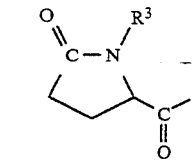  Q$^3$ and $R^1$ and $R^2$ each are independently alkyl with up to 18C atoms substituted by 1 to 3 halogen atoms or alkyl, alkenyl, alkynyl or alkadienyl groups with up to 20C atoms optionally interrupted by a 1,4-arylene group, optionally substituted by an aryl group in the ω-position and optionally substituted by an aryl-$C_{1-4}$-alkyl group, whereby $R^1$ can be interrupted by an O or S atom or by a sulphinyl or sulphonyl group in a position other than the a-position to an unsaturated C atom, or $R^1$ is an aryl—NH— or aryl—$C_{1-4}$-alkyl—OCONH— group, $R^3$ and $R^4$ each are independently hydrogen or $C_{1-4}$-alkyl or together with the N atom to which they are attached form a saturated 3- to 6-membered ring optionally containing an O or S atom in a position other than the a-position to the N atom, n is the number 1 or 0, X is an alkylene group which contains up to 6C atoms, which is optionally interrupted by an O or S atom or by a sulphinyl or sulphonyl group and which is optionally substituted by a hydroxy, mercapto, aryl, aryloxy, arylthio, aryl-$C_{1-4}$-alkyl, aryl-$C_{1-4}$-alkoxy, aryl-$C_{1-4}$-alkylthio, aryl-$C_{1-4}$-alkylidene, $C_{3-7}$-cycloalkylidene or $C_{1-6}$-alkylidene group or by one or two $C_{1-6}$-alkyl, $C_{1-6}$-alkoxy or $C_{1-6}$-alkylthio groups whereby two $C_{1-6}$-alkyl, $C_{1-6}$-alkoxy or $C_{1-6}$-alkylthio groups on the same C atom or on two adjacent C atoms can form an optionally mono-unsaturated 3- to 7-membered ring and an optionally present hydroxy or mercapto group or an optionally present unsaturated C atom must be in a position other than the a-position to an optionally present O or S atom or to an optionally present sulphinyl or sulphonyl group, or X is a group of the formula
=CHN(R,R$^o$) or —CHN(R,R$^o$)CH$_2$— where R and R$^o$ each are independently hydrogen $C_{1-4}$-alkyl, $C_{1-4}$-alkyl(CO or OCO)—, aryl, aryl(CO or OCO)—, aryl-$C_{1-4}$-alkyl or aryl-$C_{1-4}$-alkyl(CO or OCO)— and X' is an alkylene group containing up to 6C atoms which can be substituted by a $C_{1-4}$-alkoxy, aryl, aryloxy, arylthio, aryl-$C_{1-4}$-alkyl, aryl-$C_{1-4}$-alkoxy or aryl-$C_{1-4}$-alkylthio group or by one or two $C_{1-6}$-alkyl groups, whereby two $C_{1-6}$-alkyl groups attached to adjacent C atoms can form a 3- to 7-membered ring.

The alkyl, alkenyl and alkadienyl groups can be straight-chain or branched. Methyl, ethyl, propyl, i-propyl, butyl, i-butyl pentyl, hexyl, undecyl and heptadecyl are examples of alkyl groups. The respective unsaturated alkenyl and alkadienyl analogs of the alkyl groups are examples of the alkenyl and alkadienyl groups, respectively.

"Aryl" and "arylene" denote phenyl and, respectively, phenylene or phenyl and, respectively, phenylene substituted by up to 5 halogen atoms or up to 3 $C_{1-4}$-alkyl, $C_{1-4}$-alkoxy or nitro groups.

"Halogen" denotes fluorine, chlorine, bromine, and iodine.

Preferred compounds of formula I are those in which Q is a group $Q^1$, $R^1$ and $R^2$ each are independently alkyl, alkenyl or alkadienyl groups with up to 20C atoms optionally interrupted by a 1,4-phenylene group, optionally substituted by a phenyl group in the ω-position and optionally substituted by a phenyl-$C_{1-4}$-alkyl group, whereby $R^1$ can be interrupted by an O or S atom in a position other than the G-position to an unsaturated C atom, X is an alkylene group, which contains up to 6C atoms, which is optionally interrupted by an O or S atom and which is optionally substituted by a hydroxy, mercapto, phenyl, phenoxy, phenylthio, phenyl-$C_{1-4}$-alkyl, phenyl-$C_{1-4}$-alkoxy, phenyl-$C_{1-4}$-alkylthio, phenyl-$C_{1-4}$-alkylidene, $C_{3-7}$-cycloalkylidene or $C_{1-6}$-alkylidene group or by one or two $C_{1-6}$-alkyl, $C_{1-6}$-alkoxy or C1-6-alkylthio groups, whereby two $C_{1-6}$-alkyl, $C_{1-6}$-alkoxy or C1-6-alkylthio groups attached to the same C atom can form a 3- to 7-membered ring and an optionally present hydroxy or mercapto group must be in a position other than the α-position to an optionally present O or S atom, or X is a group =CHN(R,R$^o$), R and R$^o$ each are independently hydrogen, $C_{1-4}$-alkyl, $C_{1-4}$-alkyl-(CO or OCO)—, phenyl or phenyl-(CO or OCO)— and n, $R^3$ and $R^4$ are defined above.

Further preferred compounds of formula I, wherein Q is a group $Q^1$, are those in which $R^1$ and $R^2$ each are independently alkyl, alkenyl, alkynyl or alkadienyl groups with up to 20C atoms optionally substituted by an aryl group in the ω-position, whereby $R^1$ can be interrupted by a S atom in a position other than the α-position to an unsaturated C atom, or $R^1$ is anilino, alkyl with up to 18C atoms substituted by a halogen atom or a phenyl-$C_{1-4}$-alkyl—OCONH— group, $R^3$ and $R^4$ each are independently hydrogen or $C_{1-4}$-alkyl or together with the N atom to which they are attached form a saturated 6-membered ring containing an O or S atom in a position other than the a-position to the N atom, n is the number 1 or 0, X is an alkylene group, which contains up to 6C atoms, which is optionally interrupted by an O or S atom or by a sulphinyl group and which is optionally substituted by one or two $C_{1-6}$-alkyl or $C_{1-6}$-alkoxy groups, whereby two $C_{1-6}$-alkyl or $C_{1-6}$-alkoxy groups attached to the same C atom or to two adjacent C atoms can form an optionally mono-unsaturated 3- to 7-membered ring, or X is a group =CHN(R,R$^o$) or —CHN(R,R$^o$)CH$_2$— and R and R$^o$ each are independently hydrogen, $C_{2-5}$-alkanoyl or benzyloxycarbonyl.

There are further preferred the compounds of formula I in which Q is a group $Q_2$, $R^1$ and $R^2$ each are independently $C_{1-20}$-alkyl, $R^3$ and $R^4$ each are hydrogen and X' is an alkylene group containing up to 6C atoms which can be substituted by a $C_{1-4}$-alkoxy group or by one or two $C_{1-6}$-alkyl groups, whereby two $C_{1-6}$-alkyl groups attached to adjacent C atoms can form a 3- to 7-membered ring.

The compounds of formula I in which Q is a group $Q^3$, $R^3$ is hydrogen and $R^1$ and $R^2$ each are independently $C_{1-20}$-alkyl, especially hexyl or undecyl, are also preferred.

Especially preferred among the compounds of formula I in which Q is a group $Q^1$ are those in which $R^1$ is methyl, ethyl, propyl, hexyl, 2-butenyl, 3-methyl-2-butenyl, 2-propynyl, methylthio, pentylthio, 5-chloropentyl, benzyl, phenylthio, benzylthio, pentafluorobenzyl, anilino or benzyloxycarbonylamino, $R^2$ is undecyl, heptadecyl or 8,11-heptadecadienyl, $R^3$ and $R^4$ each are independently hydrogen, methyl or isopropyl or together with the N atom form a morpholino or thiomorpholino group, n is the number 1 or 0 and X is the group —(CH$_2$)$_{1-8}$—, ethylidene, propylidene, isopropylidene, butylidene, isobutylidene, pentylidene, isopentylidene, t-butylmethylene, dimethylvinylidene, cyclopentylidene, cyclohexylidene, phenethylidene, phenylpropylidene, 1,2-cyclohexylene, cyclohex-3-en-1,6-ylene, acetamidomethylene, benzyloxycarbonylaminomethylene, 1-benzyloxycarbonylamino-1,2-ethylene, methyleneoxymethylene, methylenethiomethylene, methylenesulphinylmethylene, ethylenethioethylene, ethylenesulphinylethylene, methoxymethylene or ethylene- or propylenedioxymethylene.

Especially preferred among the compounds of formula I in which Q is a group $Q^2$ are those in which $R^1$ is hexyl, $R^2$ is undecyl and X' is ethylene, 1-methoxy-1,2-ethylene or 1,2-cyclohexylene.

The following are examples of such compounds:
(S)-1-[[(2S,3S)-3-Hexyl-4-oxo-2-oxetanyl]methyl]-dodecyl-(S)-2-isopropylmalonamate,
(S)-1-[[(2S,3S)-3-hexyl-4-oxo-2-oxetanyl]methyl]-dodecyl-(S or R)-2-carbamoylvalerate,
(all Z,S)-1-[[(2S,3S)-3-ethyl-4-oxo-2-oxetanyl]methyl]-9,12-octadecadienyl-(S)-2-isopropylmalonamate,
(S)-1-[[(2S,3S or 2R,3R)-4-oxo-3-pentylthio-2-oxetanyl]-methyl]dodecyl-(S)-2-isopropylmalonamate,
(S)-1-[[(2S,3S or 2R,3R)-4-oxo-3-pentylthio-2-oxetanyl]methyl]dodecy-[S:R(2:1)]-2-isopropylmalonamate,
(S)-1-[[(2S,3S)-3-ethyl-4-oxo-2-oxetanyl]methyl]octadecyl-(S or R)-2-t-butylmalonamate,
(S)-1-[[(2S,3S)-3-ethyl-4-oxo-2-oxetanyl]methyl]octadecy-1-carbamoylcyclopentanecarboxylate, (S)-1-[[(2S,3S)-3-hexyl-4-oxo-2-oxetanyl]methyl]-dodecyl-(RS)-2-benzylmalonamate, (S)-1-[[(2S,3S)-3-hexyl-4-oxo-2-oxetanyl]methyl]-dodecyl-3-[(2-carbamoylethyl)thio]propionate, 5-oxo-D-proline-(S)-1-[[(2S,3S)-3-ethyl-4-oxo-2-oxetanyl]methyl]octadecyl ester, 5-oxo-L-proline-(S)-1-[[(2S,3S)-3-ethyl-4-oxo-2-oxetanyl]methyl]octadecyl ester and especially (S)-1-[[(2S,3S)-3-hexyl-4-oxo-2-oxetanyl]methyl]-dodecyl-(S or R)-2-isopropylmalonamate, (S)-1-[[(2S,3S)-3-hexyl-4-oxo-2-oxetanyl]methyl]-dodecyl-(RS)-2-carbamoylvalerate (epimers 1:1), (all Z,S)-1-[[(2S,3S)-3-ethyl-4-oxo-2-oxetanyl]methyl]-9,12-octadecadienyl-(S or R)-2-isopropylmalonamate, (S)-1-[[(2S,3S)-3-hexyl-4-oxo-2-oxetanyl]methyl]-dodecyl-(RS)-2-carbamoyl-4-methylvalerate (epimers 1:1), (S)-1-[[(2S,3S)-3-hexyl-4-oxo-2-oxetanyl]methyl]-dodecyl-1-carbamoylcyclohexanecarboxylate, (S)-1-[[(2S,3S)-3-hexyl-4-oxo-2-oxetanyl]methyl]-dodecyl-(RS)-2-methylmalonamate (epimers 1:1), (S)-1-[[(2S,3S)-3-hexyl-4-oxo-2-oxetanyl]methyl]-dodecyl-(RS)-2-ethylmalonamate (epimers 1:1), (S)-1-[[(2S,3S)-3-hexyl-4-oxo-2-oxetanyl]methyl]-dodecyl-(RS)-2-butylmalonamate (epimers 1:1), (S)-1-[[(2S,3S)-3-ethyl-4-oxo-2-oxetanyl]methyl]-octadecyl-1-carbamoylcyclohexanecarboxylate, (S)-1-[(2S,3S or 2R,3R)-4-oxo-3-pentylthio-2-oxetanyl]methyl]dodecyl-[S:R or R:S(2:1)]-2-isopropylmalonamate and (S)-1-[[(2R,3R)-3-benzyl-4-oxo-2-oxetanyl]methyl]-dodecyl-(S or R)-2-isopropylmalonamate.

The compounds of formula I contain at least three asymmetric C atoms and can accordingly be present as optically active enantiomers, as mixtures thereof, for example as racemates, or a diastereomers.

The compounds of formula I can be manufactured in a manner known to those of ordinary skill in the art by a) esterifying an alcohol of the formula

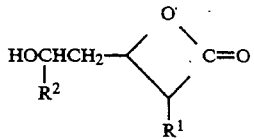

with an acid of the formula $Q^a$—OH, wherein $Q_a$ is a group of the formula $Q^1$ or $Q^3$, or b) cyclizing an acid of the formula (Q—O,R²)CHCH₂CH(OH)CH(R¹)—COOH   IIb or c) converting the carboxy group in the group T in an acid of the formula

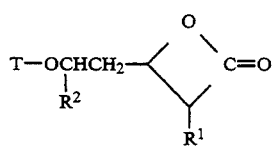

wherein T is a group of the formula

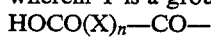   T¹ or

   T², into an amide group $(R^3, R^4)NCO$—, where $R^1$, $R^2$, $R^3$, $R^4$, X, X' and n are defined hereinabove, and d) if desired, separating a mixture of epimers of formula I into the individual epimers.

The esterification a) can be carried out in the presence of triphenylphosphine and an azodicarboxylic acid diester such as the di-t-butyl ester of diisopropyl ester in a solvent, for example an ether such as tetrahydrofuran (THF), at room temperature (~20°) or while cooling, for example to about 0° to −5° C.

The cyclization b) can be carried out in a solvent such as methylene chloride, dimethylformamide (DMF) or acetonitrile using a molecular sieve, for example in the presence of 2-(1H-benzotriazol-1-yl)-1,1,3,3-tetramethyluronium hexafluorophosphate (HBTU) and of a base such as triethylamine at room temperature (~20°) or at a temperature up to about 50° C.

The amidation c) can be carried out using a solution of ammonia or of an amine of the formula $(R^3,R^4)NH$, for example in acetonitrile, in the presence of HBTU at room temperature (~20°) or at a temperature up to about 40° C.

The optional separation of a mixture of epimers of formula I can be carried out for example by chromatography over silica gel with ethyl acetate/hexane/methylene chloride as the eluting agent.

The alcohols of formula IIa are known, for example from European Patent Application No. 0 185 359 A2, or can be prepared in analogy to the known alcohols of formula IIa or as described in Examples A to I, M and O to T.

The acid starting materials of formulae IIb and IIc were prepared in a manner known to those skilled in the art for example starting from corresponding alcohols of formula IIa as described hereinafter in Examples J and K (for the acids IIb) and K, L, and N (for the acids IIc).

EXAMPLE A a) 465 g of methyl acetoacetate and then 458 g of ethyl bromide were added under nitrogen to 720 g of 30% sodium methylate solution. The reaction mixture was subsequently boiled at reflux. After distilling off the methanol the residue was poured onto ice-water, the mixture was then extracted with n-hexane and water. The organic phases were combined and dried. After evaporation of the solvent and distillation there were obtained 328 g of methyl 2-acetylbutyrate, b.p. 77°-79°/15 Torr.

b) 144.17 g of the methyl ester from a) were added under argon at 0°-5° C. to a suspension of 26.4 g of sodium hydride in 1250 ml of THF. After stirring at 0°-5° C. for 1.5 hours the mixture was cooled to −10° C. At this temperature there were added 675 ml of 1.56M butyllithium in hexane. After stirring at −10° C. for 30 minutes a solution of 149.3 g of methyl stearate in 250 ml of THF was added dropwise. After stirring at −10° C. for 1.5 hours the reaction solution was added under argon to 250 ml of 37% hydrochloric acid and 300 g of ice. The mixture was extracted with hexane and water. The combined organic phases were dried, filtered and evaporated.

The residue was dissolved in 2500 ml of THF, treated with 76.1 g of 1,8-diazabicyclo[5.4.0]undec-7-ene(1.5-5) (DBU) and boiled at reflux under argon. The cooled reaction solution was extracted with 37% hydrochloric acid and then with saturated sodium chloride solution. The combined organic phases were dried and evaporated. The product was dissolved in ethyl acetate. The solution was cooled to room temperature and stirred at 25° C. overnight. The crystallizate was filtered off under suction, washed with ethyl acetate and dried. There were obtained 122.5 g of 3-ethyl-6-heptadecyl-4-hydroxy-2H-pyran-2-one, m.p. 101°–102° C.

c) 100 g of Raney-nickel and 2000 ml of THF were added to 100 g of the pyrone from b). After hydrogenation at 25° for 3 days the catalyst was filtered off under suction and washed with THF. The filtrate was evaporated to dryness. The residue was dissolved in ethyl acetate and stirred at 10° for 17 hours. The crystallizate is filtered off under suction, washed with cold (−10°) ethyl acetate and dried at 40° for 17 hours. There were obtained 90.54 g of rac-(2RS,2RS,5SR)-2-ethyl-5-heptadecyl-3-hydroxy-d-valerolactone, m.p. 101°–102° C.

d) 138.5 g of benzoic anhydride and subsequently 2.5 ml of 70% perchloric acid were added to a suspension of 191.3 g of the d-lactone from c) in 1250 ml of toluene. After stirring for 2.5 hours the reaction mixture was extracted in toluene with 1N sodium hydroxide solution in 20% sodium chloride solution and then with saturated sodium chloride solution. The organic phases were combined, dried and evaporated. There were obtained 243.4 g of rac-(2RS,3RS,5SR)-3-benzoyloxy-2-ethyl-5-heptadecyl-d-valerolactone, m.p. 64.5°–66° C.

e) 243 g of the benzoate from d) were dissolved in 450 ml of toluene at 40° C. under argon. 1000 ml of methanol and thereafter 2.5 ml of conc. sulphuric acid were added and the reaction mixture was stirred at 25° C. for 20 hours. After neutralization of the sulphuric acid with triethylamine the solvent was evaporated. The residue was dissolved in t-butyl methyl ether and washed with water. The aqueous phase was extracted with t-butyl methyl ether and the organic phases were combined and dried over sodium sulphate, the drying agent was filtered off under suction and washed with t-butyl methyl ether and subsequently evaporated. There were obtained 257 g of methyl rac(2RS,3R S, 5S R)-3-benzoyloxy-2-ethyl-5-hydroxydocosanoate.

f) 257 g of the hydroxyester from e) in 1250 ml of n-hexane were treated under argon with 152 g of benzyl 2,2,2-trichloroacetimidate. Then, 3.2 ml of trifluoromethanesulphonic acid were added. After stirring for 18 hours the precipitate was filtered off under suction and washed with n-hexane. The filtrate was extracted with 5% sodium bicarbonate solution and water. The combined hexane phases were dried, filtered and concentrated. After stirring at −20° C. for 20 hours the crystallizate was filtered off under suction, washed with n-hexane and discarded. The filtrate was evaporated. There were obtained 239.6 g of methyl rac(2RS,3RS,5SR)-3-benzoyloxy-5-benzyloxy-2-ethyl-docosanoate.

g) 239.6 g of the benzyl ether from f) were treated under argon with a solution of 140 g of potassium hydroxide in 1250 ml of 95% (v/v) methanol/water and stirred at 40° C. for 17 hours. Subsequently, the mixture was concentrated at 40° C., the suspension was taken up in t-butyl methyl ether and washed in sequence with 10% sodium chloride solution, 1N hydrochloric acid and again with 10% sodium chloride solution. The organic phase was dried with sodium sulphate, the drying agent was filtered off under suction and washed with t-butyl methyl ether. The filtrate was evaporated. There were obtained 182.1 g of rac-(2RS,3RS,5SR)-5-benzyloxy-2-ethyl-3-hydroxydocosanoic acid.

h) 33.3 g of (S)-(−)-a-methylbenzylamine were added to a solution of 182.1 g of the b-hydroxyacid from g) in 1250 ml of methyl acetate. The solution was seeded with 50 mg of the phenethylamine salt of (2S,3S,5R)-5-benzyloxy-2-ethyl-3-hydroxydocosanoic acid and left to stand for 20 hours. The crystallizate was filtered off under suction, washed with cold (−20° C.) methyl acetate and then dried. This 1st crystallizate was dissolved in hot methyl acetate, cooled to 45° C. and seeded with 50 mg of the phenethylamine salt of (2S,3S,5R)-5-benzyloxy-2-ethyl-3-hydroxydocosanoic acid. The solution was left to stand at room temperature or 20 hours. The crystallizate was filtered off under suction, washed with cold (−20° C.) methyl acetate and dried. The same procedure as with the 1st crystallizate was repeated with the 2nd crystallizate. There were obtained 39.4 g of the phenethylamine salt of (2S,3S,5R)-5-benzyloxy-2-ethyl-3-hydroxydocosanoic acid, m.p. 92°–95° C.

i) 39.4 g of the phenethylamine salt from h) were treated with 400 ml of t-butyl methyl ether and 80 ml of 1N hydrochloric acid and dissolved while stirring. The organic phase was washed with water, dried, filtered and concentrated. There was obtained 31.4 g of (2S,3S,5R)-5-benzyloxy-2-ethyl-3-hydroxydocosanoic acid, m.p. 62°–63.5° C.

j) 17.6 g of benzenesulphonyl chloride were added dropwise at 0° C. under argon to a solution of 24.5 g of the b-hydroxyacid from i) in 250 ml of pyridine. After stirring at 0° C. for 20 hours 5 ml of water were added dropwise to the solution. The mixture was stirred at room temperature for 1 hour. The pyridine was evaporated. The crystal slurry was taken up in t-butyl methyl ether and washed in sequence with 2N hydrochloric acid, 5% sodium bicarbonate solution and 10% sodium chloride solution. The organic phase was dried over sodium sulphate and thereafter triturated with active charcoal. The drying agent and active charcoal were filtered off under suction and the filtrate was evaporated. There were obtained 23.4 g of (3S,4S)-4-[(R)-2-benzyloxynonadecyl]-3-ethyl-2-oxetanone.

k) A solution of 23.4 g of the oxetanone from j) in 250 ml of THF was treated with 2.3 g of 10% Pd/C. After hydrogenation for 5 hours the hydrogenation solution was suction filtered. After washing with THF the filtrate was evaporated, the residue was dissolved in n-hexane and seeded with (3S,4S)-3-ethyl-4-[(R)-2-hydroxynonadecyl]-2-oxetanone. After 18 hours the crystallizate was filtered off under suction, washed with hexane and dried. There were obtained 16.1 g of (3S,4S)-3-ethyl-4-[(R)-2-hydroxynonadecyl]-2-oxetanone, m.p. 66.5°–68° C., the alcohol starting material of Example 1.

EXAMPLE B a) 50 g of methyl (R)-3-hydroxytetradecanoate, 35 g of t-butyldimethylchlorosilane, 6.1 g of 4-dimethylaminopyridine and 29.4 g of triethylamine were dissolved in 200 ml of methylene chloride and stirred at room temperature for 30 hours as well as under reflux for 16 hours. Thereupon, a further 2 g of t-butyldimethylchlorosilane were added. After a further 24 hours under reflux the precipitated triethylamine hydrochloride salt was filtered off, washed with ether and the filtrate was concentrated. The residue was dissolved in ether and washed in sequence with water, 0.5M citric acid, again with water and saturated sodium chloride solution, dried, concentrated and subsequently freed from volatile material at 5° C. in a high vacuum for 5 hours. There were obtained 71.8 g of (R)-3-[(1,1-dimethylethyl)dimethylsilyloxy]tetradecanoic acid, IR (cm$^{-1}$): 1745, 1254, 895, 776.

b) 18.63 g of the product from a) dissolved in 100 ml of ether were treated with 65 ml of 1M diisobutylaluminium hydride solution in hexane at a temperature of $-70°$ C. to $-75°$ C. and then stirred at this temperature for 1 hour. Thereupon, 2.5 ml of isopropanol, 10 ml of water and 50 ml of 0.5M citric acid solution were added dropwise at a max. of 10° C. The ether phase was separated, the aqueous phase was extracted with ether, the combined ether phases were washed with brine, dried and concentrated. The residue was chromatographed on silica gel with pentane/ether (5:1) and there were obtained 14.47 g of (R)-3-[(1,1-dimethylethyl)dimethylsilyloxy]tetradecanal, IR (cm$^{-1}$): 1728, 1254, 836, 775.

c) A solution of 2.55 ml of diisopropylamine in 45 ml of THF was treated at 0° C. with 22.5 ml of a solution of 1.6M n-butyllithium in hexane and, after stirring for 15 minutes, cooled to $-75°$ C. Then, a solution of 2.9 g of pentylthioacetic acid in 9 ml of THF was added dropwise. After stirring for 10 minutes the reaction mixture was left to warm to room temperature, stirred for 5 minutes and again cooled to $-75°$ C. At this temperature there was added dropwise a solution of 2.4 g of the aldehyde from b) in 9 ml of THF. After stirring for 20 minutes the reaction mixture was poured into saturated ammonium chloride solution and extracted with hexane. The hexane phase was dried and concentrated. There were obtained 3.89 g of (2R/S,3R/S,5R)-5-[(1,1-dimethylethyl)dimethylsilyloxy]-3-hydroxy-2-pentylthiohexadecanoic acid as a mixture of 4 diastereomers.

d) A solution of 3.89 g of the product from c), 3.18 g of 2-(1H-benzotriazol-1-yl)-1,1,3,3-tetramethyluronium hexafluorophosphate (HBTU), 2 g of 4A molecular sieve and 3 ml of triethylamine was stirred for 2 hours in a mixture of 130 ml of methylene chloride and 6 ml of DMF. Thereupon, the mixture was filtered, the filtrate was concentrated, the residue was dissolved in water/methanol (3:7) and extracted with hexane. The hexane phase was dried and concentrated. There were obtained 3.57 g of (3R/S,4R/S)-4-[(R)-2-[(1,1-dimethylethyl)-dimethylsilyloxy]tridecyl]-3-pentylthio-2-oxetanone as a mixture of 4 diastereomers.

e) A solution of 4.5 g of the product from d) in 200 ml of acetonitrile was treated with 15 ml of 40% hydrofluoric acid and stirred for 18 hours. Thereupon, sodium bicarbonate solution was added, the mixture was then extracted with hexane and the hexane phase was dried and concentrated. The residue was chromatographed on silica gel with 1-5% ether in methylene chloride. There were obtained 699.9 mg of 3R,4R (or 3S,4S)-4[(R)-2-hydroxytridecyl]-3-pentylthio-2-oxetanone, m.p. 43° C., and 691.2 mg of 3S,4S (or 3R,4R)-4-[(R)-2-hydroxytridecyl]-3-pentylthio-2-oxetanone, m.p. 71° C., the alcohol starting materials of Examples 5 and 6.

EXAMPLE C a) 18 ml of a 1M solution of lithium bis(trimethylsilyl)amide in THF were treated with 1.8 ml of ethyl acetate under argon at $-75°$ C., stirred at this temperature for 30 minutes and subsequently treated with 4.8 g of (R)-3-benzyloxytetradecanal in 15 ml of THF and stirred at $-78°$ C. for half an hour. A solution of 3.8 ml of conc. hydrochloric acid in 6 ml of water was added dropwise to the reaction mixture. The solution obtained was extracted with ethyl acetate, the combined organic phases were washed with 10% sodium bicarbonate and water, dried, filtered and concentrated. There was obtained ethyl (3R,5R and 3S,5R)-5-benzyloxy-3-hydroxyhexadecanoate (1:1).

b) A solution of 4 ml of diisopropylamine in 12.5 ml of THF was treated with 17 ml of a 1.6M solution of n-buli in n-hexane under argon at 0° C. After stirring for 15 minutes 5 g of the product from a) in 2.5 ml of THF were added dropwise at $-50°$ C. After 10 minutes at $-10°$ C. the temperature was lowered to $-50°$ C. and, after the dropwise addition of a solution of 3.18 g of benzyl bromide in 3.1 ml of hexamethylphosphoric acid triamide, the mixture was stirred at $-50°$ C. for 15 minutes. Thereafter, the cooling bath was removed and the reaction mixture was stirred at room temperature for 3 hours. The reaction mixture was cooled to 0° C. and 50 ml of saturated sodium chloride solution were added thereto, the mixture was extracted with t-butyl methyl ether, the extracts are dried, filtered and the solvent was evaporated. The residue was chromatographed on silica gel with n-hexane/ethyl acetate (4:1). The residue was dried. There was obtained ethyl (2R,3R,5R and 2S,3S,5R)-5-benzyloxy-2-benzyl-3-hydroxyhexadecanoate as 1:1 threo diastereomers.

c) A solution of 3.1 g of the product from b) and 26 ml of 2.5N sodium hydroxide solution in 37.2 ml of ethanol was heated at reflux for 50 minutes and subsequently neutralized at room temperature with 26 ml of 2.5N hydrochloric acid. The ethanol was distilled off, whereupon the residue was extracted with t-butyl methyl ether and water. The combined organic phases were dried and concentrated. A solution of 3 g of the residue in 109 ml of methylene chloride was stirred under argon and treated with 2.59 g of HBTU and 2.74 g of molecular sieve. Subsequently, 5.5 ml of DMF and 2.8 ml of triethylamine were added and the reaction mixture was stirred for 1 hour, filtered and concentrated. The residue was taken up in n-hexane, the solution was thereupon extracted with water, dried and concentrated in a vacuum. Chromatography on silica gel with methylene chloride gave a 1st trans diastereomer (3S,4S or 3R,4R)-3-benzyl-4-[(R)-2-benzyl- oxytridecyl]-2-oxetanone, Rf value: 0.45 (thin-layer chromatography over silica gel 5–40 m with methylene chloride) and a 2nd trans diastereomer, (3R,4R or 3S,4S)-3-benzyl-4-[(R)-2-benzyloxytridecyl]-2-oxetanone, Rf value: 0.50 (thin-layer chromatography over silica gel 5–40 m with methylene chloride).

d) A solution of 646 mg of the 2nd trans diastereomer from c) in 65 ml of THF was hydrogenated for 1 hour in the presence of 646 mg of 10% Pd/C. The reaction mixture was filtered and concentrated. There was obtained a trans diastereomer: (3R,4R or S,4S)-3-benzyl-4-[(R)-2-hydroxytridecyl]-2-oxetanone, the alcohol starting material in Example 7.

e) As described under d), from the 1st trans diastereomer from c) there was obtained the trans diastereomer: (3S,4S or 3R,4R)-3-benzyl-4-[(R)-2-hydroxytridecyl]-2-oxetanone, the alcohol starting material in Example 8.

EXAMPLE D

A solution of 3.0 ml of diisopropylamine in 50 ml of THF was treated at 0° C. with 12.0 ml of a solution of 1.6M n-butyllithium in hexane and, after stirring, cooled to $-75°$ C. A solution of 1.26 g of Z-glycine in 10 ml of THF was then added dropwise. The reaction mixture was left to warm to room temperature and again cooled to $-75°$ C. 0.7 g of (R)-3-(t-butyldimethylsiloxy)tetradecanal in 5 ml of THF was then added dropwise at −75° C. The reaction mixture was stirred at −75° C. for 1 hour and at −40° to −50° C. for ½ hour, then warmed to 5° C., again cooled to −75° C., poured into dilute potassium hydrogen sulphate solution and extracted with ether. The ether phase was dried, concentrated and chromatographed on silica gel with methylene chloride/methanol. There were obtained 540 mg of (2R/S,3R/S,5R)-2-[1 -(benzyloxy)formamido]-5-(t-butyldimethylsiloxy)-3-hydroxyhexadecanoic acid as a mixture of 4 diastereomers.

In analogy to Example Bd), from the above product there was obtained benzyl 4-[(R)-2-(t-butyldimethylsiloxy)tridecyl]-2-oxo-3-oxetanecarbamate as a 1:1 mixture of the two transdiastereomeric β-lactones, MS: 476 (M+--C$_4$H$_9$·).

In analogy to Example Be), from the above mixture there were obtained (3S,4S or 3R,4R)-benzyl 4-[(R)-2-hydroxytridecyl]-2-oxo- 3-oxetanecarbamate, the alcohol starting material in Example 15, m.p. 122°–124° C., and (3R,4R or 3S,4S)-benzyl-4-[(R)-2-hydroxytridecyl]-2-oxo-3-oxetanecarbamate, m.p. 98°–99° C.

EXAMPLE E

In analogy to Example B, from thiophenoxyacetic acid and (R)-3-[(1,1 -dimethylethyl)dimethylsilyloxy]-tetradecanal there was obtained, via
 a) (2R/S,3R/S,5R)-5-(t-butyldimethylsiloxy)-3-hydroxy-2-(phenylthio)hexadecanoic acid (mixture of 4 diastereomers) and
 b) (3R/S,4R/S)-4-[(R)-2-(t-butyldimethylsiloxy)tridecyl]-3-(phenylthio)-2-oxetanone (mixture of 4 diastereomers), IR (cm$^{-1}$): 2927, 2855, 1833, 1254, (3S,4S)-4-[(R)-2-hydroxytridecyl]-3-(phenylthio)-2-oxetanone m.p. 79° C. (ether), and (3R,4R)-4-[(R)-2-hydroxytridecyl]-3-(phenylthio)-2-oxetanone, m.p. 47° C. (ether), the alcohol starting material of Example 16.

EXAMPLE F a) 270 ml of stearoyl chloride were added dropwise at a maximum of 150° C. to a solution of 117 g of Meldrum's acid and 131 ml of pyridine in 1.5 l of methylene chloride. After stirring the reaction mixture was washed with 4N hydrochloric acid, the aqueous phase was back-extracted with methylene chloride and the methylene chloride phase was dried and concentrated. The residue was taken up in methanol and stirred under reflux. After cooling the separated crystals were filtered off, dissolved in methylene chloride and chromatographed on silica gel with methylene chloride. There were obtained 175 g of methyl 3-oxoeicosanoate, m.p. 52°–54° C.

b) 1.84 mg of acetyl chloride in 1.84 ml of methanol were added to a solution of 9.1 mg of [(R)-2,2′-bis(diphenylphosphino)-6,6′-dimethylbiphenyl]ruthenium diacetate in 20 ml of methylene chloride. The solution obtained was hydrogenated at 35 bar of hydrogen and 60° C. together with 39.8 g of the ketoester from a) and 170 ml of methanol. After the addition of methylene chloride the mixture was evaporated to dryness. Chromatography on silica gel with ether and recrystallization from n-hexane yielded 35.6 g of methyl (R)-3-hydroxyeicosanoate, m.p. 64°–64.5° C.

c) Analogously to Example B, from the product of b) there were obtained, via
 methyl (R)-3-(t-butyldimethylsiloxy)eicosanoate, IR (cm$^{-1}$): 1745, 1255, 836,
 (R)-3-(t-butyldimethylsiloxy)eicosanal, IR (cm$^{-1}$): 1728, 1463, 1255, 1104, 836, 775, (2R/S,3R/S,5R)-5-(t-butyldimethylsiloxy)-3-hydroxy-2-(methylthio)docosanoic acid (mixture of 4 diastereomers), MS: 533 (M+H)+,
 4-[(R)-2-(t-butyldimethylsiloxy)nonadecyl]-3-(methylthio)-2-oxetanone, (1:1 mixture of two trans diastereomers), IR (cm$^{-1}$): 1834, 1463, 1256, 1106, 836, and
 4-[(R)-2-(t-butyldimethylsiloxy)nonadecyl]-3-(methylthio)-2-oxetanone (1:1 mixture of two cis diastereomers), IR (cm$^{-1}$): 1834, 1463, 1256, 1106, 1066, 836,
 the following alcohol starting materials of Example 17:
 (3S,4R or 3R,4S)-4-[(R)-2-Hydroxynonadecyl]-3-(methylthio)-2-oxetanone, m.p. 65° C. (from methylene chloride)
 (3R,4S or 3S,4R)-4-[(R)-2-hydroxynonadecyl]-3-(methylthio)-2-oxetanone, m.p. 67° C. (from methylene chloride)
 (3R,4R or 3S,4S)-4-[(R)-2-hydroxynonadecyl]-3-(methylthio)-2-oxetanone, m.p. 71° C. (from ether) and
 (3S,4S or 3R,4R)-4-[(R)-2-hydroxynonadecyl]-3-(methylthio)-2-oxetanone, m.p. 80° C. (from ether).

EXAMPLE G

Analogously to Example B, from (benzylthio)-acetic acid and (R)-3-[(1,1-dimethylethyt)dimethylsilyloxy]-tetradecanal there was obtained, via
 (2 R/S,3R/S,5R)-2-(benzylthio)-5-[(1,1-di-methylethyl)dimethylsilyloxy]-3-hydroxyhexadecanoic acid (mixture of 4 diastereomers) and
 (3R/S,4R/S)-3-(benzylthio)-4-[(R)-2-(t-butyldimethylsiloxy)tridecyl]-2-oxetanone (mixture of 4 diastereomers), MS: 506 (M+),
 the following alcohol starting materials of Examples 19 and 20:
 (3S,4S or 3R,4R)-3-(Benzylthio)-4-[(R)-2-hydroxytridecyl]-2-oxetanone, m.p. 65° C. (ether),
 (3R,4R or 3S,4S)-3-(benzylthio)-4-[(R)-2-hydroxytridecyl]-2-oxetanone, MS: 374 (M+--H$_2$O), and
 (3R,4S and 3S,4R)-3-(benzylthio)-4-[(R)-2-hydroxytridecyl]-2-oxetanone (1:1 diast.), MS: 374 (M+--H$_2$O).

EXAMPLE H a) 104 g of the mother liquor from the 1st crystallization in Example Ah) were dissolved in water and methylene chloride. The mixture was acidified to pH1 by the addition of conc. HCl while cooling with ice, the methylene chloride phase was separated, the aqueous phase was extracted with methylene chloride and the methylene chloride phase was washed with water, dried and concentrated. There were obtained 86.7 g of enriched (2R,3R,5S)-5-benzyloxy-2-ethyl-3-hydroxydocosanoic acid which were dissolved in 500 ml of ethyl acetate and treated with 20.6 g of (R)-(+)-a-methylbenzylamine while cooling. After the addition of ethyl acetate the mixture was heated to reflux, filtered and crystallized-out. The crystals obtained were recrystallized from ethyl acetate and methyl acetate. There were obtained 70.0 g of the phenethylamine salt of (2R,3R,5S)-5-benzyloxy-2-ethyl-3-hydroxydocosanoic acid, m.p. 88°–91° C.

b) Analogously to Examples Ai), j), and k), from the above salt there is obtained, via
 (2R,3R,5S)-5-benzyloxy-2-ethyl-3-hydroxydocosanoic acid m.p. 61.5°–63° C., and
 (3R ,4R)-4-[(S)-2-benzyloxynonadecyl]-3-ethyl-2-oxetanone, m.p. 38°–40° C.

(3R  ,4R)-3-ethyl-4-[(S)-2-hydroxynonadecyl]-2-oxetanone, m.p. 66°-68° C.

c) A solution of 14.2 g of the product obtained and 8.65 g of triphenylphosphine in 250 ml of THF was treated at +5° C. with 1.19 ml of formic acid and then with a solution of 5.12 g of diethyl azodicarboxylate in 20 mi of THF. The mixture was then again treated with 0.4 ml of formic acid, 2.9 g of triphenylphosphine and 1.7 ml of diethyl azodicarboxylate. The reaction mixture was concentrated and the residue was chromatographed on silica gel with hexane/ethyl acetate; there were obtained 13.1 g of (R)-1-[[(2R,3R)-3-ethyl-4-oxo-2-oxetanyl]methyl]octadecyl formate.

The product obtained was dissolved in 150 ml of methanol and treated at 15° C. with 0.114g of p-toluenesulphonic acid monohydrate. After stirring the reaction mixture was concentrated, the residue was partitioned between methylene chloride and aqueous sodium bicarbonate and extracted with methylene chloride. The methylene chloride phase was dried and concentrated and the residue was recrystallized from ethyl acetate. There were obtained 9.5 g of (3R,4R)-3-ethyl-4-[(R)-2-hydroxynonadecyl]-2-oxetanone, m.p. 80°-82° C., the alcohol starting material in Example 21.

EXAMPLE I a) 187.5 ml of n-butyllithium solution (1.6M in hexane) were added dropwise at −20° C. to a solution of 42.5 ml of diisopropylamine in 500 ml of THF. After stirring the solution was added dropwise at a maximum of −65° C. to a suspension of 39.9 g of (S)-(−)-2-hydroxy-1,2,2-triphenylethyl-acetate in 600 ml of THF. Then, the reaction mixture was warmed to 0° C., stirred, cooled to −70° C. and treated with a solution of 51.2 g of (R)-3-[(t-butyl)- dimethylsilyloxy]eicosanal in 400 ml of THF. After stirring 500 ml of saturated ammonium chloride solution were added dropwise, the mixture was then warmed to room temperature and stirred. The reaction mixture was concentrated, partitioned between water and ether and extracted with ether, the ether phase was washed with water, concentrated, taken up in 1 l of methylene chloride, dried and concentrated. There were obtained 91.9 g of (S)-2-hydroxy-1,2,2-triphenylethyl [3R:3S(4:1),5R]-5-(t-butyldimethylsiloxy)-3-hydroxydocosanoate, IR (cm$^{-1}$): 3525, 1719. 1448, 1250, 1159, 838, 697.

b) A solution of 90.8 g of the product obtained above in 1 l of methanol was treated with 22.15 ml of 5.4M sodium methylate in methanol. After stirring the solution was concentrated, the residue was partitioned between ether and saturated ammonium chloride solution and extracted with ether. The ether phase was dried, concentrated and chromatographed on silica gel with hexane/ethyl acetate. There were obtained 42.7 g of methyl (3R,5R)-5-(t-butyldimethylsiloxy)-3-hydroxydocosanoate, IR (cm$^{-1}$): 3521. 3468, 1738, 1254, 1168, 1137, 1105.

c) Analogously to Examples Be) and Cb), and c), the latter compound was converted, via methyl (2R,3R,5R)-5-(t-butyldimethylsiloxy)-3-hydroxy-2-methyldocosanoate, IR (cm$^{-1}$): 3522, 1739, 1464, 1254, 1066, and (3R,4R)-4-[(R)-2-(t-butyldimethylsilyloxy)-nonodecyl]-3-methyl-2-oxetanone, IR (cm$^{-1}$): 1830, 1464, 1254, 1129, 1071, into (3R,4R)-4-[(R)-2-hydroxynonadecyl] -3-methyl-2-oxetanone, m.p. 82.5°-84° C. (from EtOAc/hexane), the alcohol starting material in Example 22.

EXAMPLE J a) 1.1 g of (3S,4S)-3-hexyl-4-[(R)-2-hydroxytridecyl]-2-oxetanone, 1.6 g of triphenylphosphine, 0.825 g of salicylamide and 3 g of molecular sieve (4Å) were treated with 20 ml of THF and cooled to 0° C. Thereupon, 1.4 g of di-t-butyl azodicarboxylate were added. After warming to room temperature and stirring the reaction mixture was concentrated and the residue was partitioned between methanol/water (70:30) and hexane and extracted with hexane. The hexane phase was dried and concentrated and the residue was chromatographed on silica gel with hexane/ethyl acetate (4:1). There were obtained 0.727 g of o-[[(S)-1-[[(2S,3S)-3-hexyl-4-oxo-2-oxetanyl]methyl]dodecyl]oxy]-benzamide, MS: 474 (M+H)+.

b) 972 mg of the product obtained above were dissolved in 12 ml of methanol and treated with 0.2 g of potassium carbonate. After stirring the reaction mixture was concentrated and the residue was partitioned between methanol/water (7:3) and hexane and extracted with hexane. The hexane phase was dried and concentrated. There were obtained 854 mg of methyl (2S,3S,5S)-5-(o-carbamoylphenoxy)-2-hexyl-3-hydroxyhexadecanoate, MS: 369 (M+--(o-carbamoylphenoxy)).

c) 850 mg of the product obtained above were dissolved in 12 ml of methanol/water (98:2) treated, with 800 mg of 5 percent rhodium on aluminium oxide and hydrogenated at 100° C. and 100 bar of hydrogen. The reaction mixture was filtered, concentrated and chromatographed on silica gel with hexane/ethyl acetate (1:1). There were obtained 213 mg of methyl (2S,3S,5S)-5-[[(cis)-2-carbamoylcyclohexyl]oxy]-2-hexyl-3-hydroxyhexadecanoate (1st. diast.), MS: 367 [M+--(H$_2$NCOC$_6$H$_{10}$-+H$_2$O)], 204 mg of a mixed fraction and 142 mg of methyl (2S,3S,5S)-5-[[(cis)-2-carbamoylcyclohexyl]oxy]-2-hexyl- 3-hydroxyhexadecanoate (2nd. diast.), MS: 367 [M+--(H$_2$NCOC$_6$H$_{10}$-+H$_2$O)].

d) 210 mg of the 1st diastereomer obtained above were dissolved in 10 ml of acetone and treated with 3 ml of 1N potassium hydroxide. After stirring the reaction mixture was poured into potassium hydrogen sulphate solution and extracted with ether. The ether phase was dried and evaporated. There were obtained 277 mg of (2S,3S,5S)-5-[[(cis)-2-carbamoylcyclohexyl]oxy]-2-hexyl-3-hydroxyhexadecanoic acid (1st. diast.), the acid starting material in Example 23a).

e) As described in d), from the 2nd diastereomer from c) there was obtained (2S,3S,5S)-5-[[(cis)-2-carbamoylcyclohexyl]oxy]-2-hexyl-3-hydroxyhexadecanoic acid (2nd. diast.), the acid starting material in Example 23b).

EXAMPLE K a) Analogously to Example Hc), from (3S,4S)-3-hexyl-4-[(R)-2-hydroxytridecyl]-2-oxetanone and formic acid there was obtained, via (S)-1-[[(2S,3S)-3-hexyl-4-oxo-2-oxetanyl]methyl]dodecyl formate, IR (cm$^{-1}$): 1826, 1725, 1177, 1122, (3S,4S)-3-hexyl-4-[(S)-2-hydroxytridecyl]-2-oxetanone m.p. 63°-64° C. (from hexane).

b) 1.8 g of the hydroxy-β-lactone prepared above, 1.3 g of pyridinium p-toluenesulphonate and 2 g of molecular sieve (4Å) in 10 ml of methyl 3,3-dimethoxypropionate were stirred at 100° C. under argon, the reaction mixture was then filtered, the residue was concentrated and chromatographed on silica gel with ether/methylene chloride. There were obtained 1. 213 mg of methyl (E)-3-[[(S)-1-[[(2S,3S)-3-hexyl-4-oxo-2-oxetanyl]methyl]dodecyl]oxy]acrylate, IR (cm$^{-1}$): 1827, 1714, 1643, 1622, 1192, and
2. 826 mg of methyl (R/S)-3-[[(S)-1-[[(2S,3S)-3-hexyl-4-oxo-2-oxetanyl]methyl]dodecyl]oxy]-3-methoxypropionate (1:1 epimer mixture), IR (cm$^{-1}$): 1824, 1743, 1438, 1117.

c) 235 mg of the product of b)2. were suspended in 25 ml of 0.02N NaOH and the reaction mixture was diluted with acetone. After stirring for 24 hours the mixture was acidified with 5 percent potassium hydrogen sulphate solution and extracted with ether. The ether phase was dried and concentrated and the residue was chromatographed on silica gel with methylene chloride/methanol. There were obtained 60 mg of (2S,3S,5S)-2-hexyl-3-hydroxy-5-[(R/S)-1-methoxy-2-(methoxycarbonyl)-ethoxy]hexadecanoic acid, MS: 337 (M+--(H$_2$O+—O—(CH$_3$O)—CH$_2$—COOCH$_3$)).

d) A solution of 58 mg of the above compound in 4 ml of condensed ammonia was heated at 50° C. in an autoclave. Subsequently, the ammonia gas was allowed to escape and the mixture was then treated with potassium hydrogen sulphate solution and extracted with methylene chloride. The methylene chloride phase was dried and concentrated. There were obtained 42.5 mg of (2S,3S,5S)-5-[(R/S)-2-carbamoyl-1-methoxyethoxy]-2-hexyl-3-hydroxyhexadecanoic acid, the acid starting material of Example 24.

EXAMPLE L

A solution of 200 mg of the product of Example Kb)1. in 10 ml of THF was hydrogenated using 200 mg of Pd/C (10%). Then, the mixture was filtered, the filtrate was concentrated and the residue was chromatographed on silica gel with 1% ether in methylene chloride. There were obtained 99 mg of methyl 3-[[(S)-1-[[(2S,3S)-3-hexyl-4-oxo-2-oxetanyl]methyl]dodecyl]oxy]-propionate, MS: 285 (M+--(C$_{11}$H$_{23}$Σ)).

A suspension of 544 mg of this compound in 49 ml of 0.02N sodium hydroxide was treated with acetonitrile. The resulting solution was acidified with aqueous potassium hydrogen sulphate, the reaction mixture was extracted with ether and the ether phase was dried and concentrated. Chromatography on silica gel with 2% ether in methylene chloride and then 5% methanol in methylene chloride yielded 43.7 mg of 3-[[(S)-1-[[(2S,3S)-3-hexyl-4-oxo-2-oxetanyl]methyl]dodecyl]oxy]propionic acid, IR (cm$^{-1}$): 1823, 1715, 1466, 1105, the acid starting material in Example 25.

EXAMPLE M

Analogously to Examples Cb) and c), methyl (3R,5R)-5-(t-butyldimethylsiloxy)-3-hydroxydocosanoate (Example Ib) was reacted with propargyl bromide to give methyl (2R,3R,5R)-5-(t-butyldimethylsiloxy)-3-hydroxy-2-(2-propynyl)docosanoate, IR (cm$^{-1}$): 3310, 2120, 1740, 1255, the latter was saponified to give (2R,3R,5R)-5-(t-butyldimethylsiloxy)-3-hydroxy-2-(2-propynyl)-docosanoic acid, IR (cm$^{-1}$): 3315, 2120, 1715, 1255, and this acid was cyclized to give (3R,4R)-4-[(R)-2-(t-butyldimethylsiloxy)nonadecyl]-3-(2-propynyl)-2-oxetanone, IR (cm$^{-1}$): 3315, 2130, 1830, 1255.

After cleavage of the protecting group analogously to Example Be) there was obtained (3R,4R)-4-[(R)-2-hydroxynonadecyl]-3-(2-propynyl)-2-oxetanone, m.p. 62°-63° C. (from ethyl acetate), the alcohol starting material in Example 60.

EXAMPLE N

Analogously to Example 1, from (3S,4S)-3-hexyl-4-[(R)-2-hydroxytridecyl]-2-oxetanone and monobenzyl malonate there was obtained benzyl (S)-1-[[(2S,3S)-3-hexyl-4-oxo-2-oxetanyl]-methyl]dodecylmalonate, IR (cm$^{-1}$): 1824, 1734, 1149, 1125.

A solution of 430 mg of this product in 15 ml of THF was treated with 100 mg of Pd/C and then hydrogenated. The reaction mixture was filtered and the filtrate was concentrated. There were obtained 361 mg of (S)-1-[[(2S,3S)-3-hexyl-4-oxo-2-oxetanyl] methyl]dodecyl hydrogen malonate, IR (cm$^{-1}$): 1824, 1745, the acid starting material of Example 26.

EXAMPLE O

A solution of 1.96 g of the alcohol product of Example M in 50 ml of ethyl acetate was hydrogenated using 0.25 g of 10 percent Pd/C, the reaction mixture was then filtered and the residue was chromatographed on silica gel with ethyl acetate/hexane. There were obtained 1.44 g of (3R,4R)-4-[(R)-2-hydroxynonadecyl]-3-propyl-2-oxetanone, m.p. 84°-85° C. (from ethyl acetate/hexane), the alcohol starting material in Example 61.

EXAMPLE P a) From (R)-3-(t-butyldimethylsiloxy)tetradecanal (Example Bb) there was obtained analogously to Example Ca),b),c), via ethyl (3R and 3S,5R)-5-(t-butyldimethylsiloxy)-3-hydroxyhexadecanoate (epimer mixture) and ethyl (R and S)-2-[(1R and 1S,3R)-3-(t-butyldimethylsiloxy)-1-hydroxytetradecyl]-5-methyl-4-hexenoate (1:1 threo diastereomers), (3R,4R and 3S,4S)-4-[(R)-2-(t-butyldimethylsiloxy)-tridecyl]-3-(3-methyl-2-butenyl)-2-oxetanone (1:1 trans diastereomers).

b) A solution of 1.87 g of the product of a) in 50 ml of acetonitrile was treated with 6.2 ml of 40% hydrofluoric acid. After stirring sodium bicarbonate solution was added, the mixture was then extracted with methylene chloride and the methylene chloride phase was dried and concentrated. The residue was chromatographed on silica gel with ethyl acetate/methylene chloride/n-hexane (1:4.5:4.5). The chromatography gave the alcohol starting materials for Examples 62–65:

A 1st trans diastereomer, (3S,4S)-4-[(R)-2-hydroxytridecyl]-3-(3-methyl-2-butenyl)-2-oxetanone, Rf-value: 0.31, and a 2nd trans diastereomer, (3R,4R)-4-[(R)-2-hydroxytridecyl]-3-(3-methyl-2-butenyl)-2-oxetanone Rf value: 0.26 (thin-layer chromatography over silica gel 5–40 m with ethyl acetate/methylene chloride/hexane (1:4.5:4.5)).

EXAMPLE Q

From ethyl (3R,5R and 3S,5R)-5-benzyloxy-3-hydroxyhexadecanoate (1:1) (Example Ca)) there were obtained analogously to Examples Cb) to e) via ethyl-(2R,3R,5R and 2S,3S,5R)-5-benzyl-2-(5-chloropentyl)-3-hydroxyhexadecanoate (threo diastereomers), a 1st trans diastereomer, (3S,4S or 3R,4R)-4-[(R)-2-(benzyloxy)tridecyl]-3-(5-chloropentyl)-2-oxetanone, Rf value: 0.47, and a 2nd trans diastereomer, (3R,4R or 3S,4S)-4-[(R)-2-(benzyloxy)tridecyl]-3-(5-chloropentyl)-2-oxetanone, Rf value: 0.28 (thin-layer chromatography over silica gel 5–40 m with methylene chloride), the alcohol starting materials for Examples 66–69:
(3R,4R or 3S,4S)-3-(5-chloropentyl)-4-[(R)-2-hydroxytridecyl]-2-oxetanone and
(3S,4S or 3R,4R)-3-(5-chloropentyl)-4-[(R)-2-hydroxytridecyl]-2-oxetanone.

EXAMPLE R

From (R)-3-(t-butyldimethylsiloxy)tetradecanal (Example Bb)) there were obtained analogously to Example Cb) and c) via ethyl (R and S,E)-2-[(1R and 1S,3R)-3-(t-butyldimethylsiloxy)tetradecyl]-4-hexenoate (1:1 threo diastereomers) and
(3R,4R and 3S,4S)-3-[(E)-2-butenyl]-4-[(R)-2-(t-butyldimethylsiloxy)tridecyl]-2-oxetanone (1:1 trans diastereomers), the alcohol starting materials for Examples 70–73:
A 1st trans diastereomer, (3S,4S or 3R,4R)-3-[(E)-2-butenyl]-4-[(R)-2-hydroxytridecyl]-2-oxetanone, Rf value: 0.475 and
a 2nd trans diastereomer, (3R,4R or 3S,4S)-4-[(E)-2-butenyl]-4-[(R)-2-hydroxytridecyl]-2-oxetanone, Rf value: 0.44 (chromatography and thin-layer chromatography over silica gel with ethyl acetate/methylene chloride/n-hexane (1:2:2)).

EXAMPLE S

From ethyl (3R,5R and 3S,5R)-5-benzyloxy-3-hydroxyhexadecanoate (1:1) (Example Ca))there were obtained analogously to Example Cb) and c) via ethyl (2R,3R and 2S,3S,5R)-5-(benzyloxy)-3-hydroxy-2-(2,3,4,5,6-pentafluorobenzyl)hexadecanoate (threo diastereomers) and
(3R,4R and 3S,4S)-4-[(R)-2-(benzyloxy)tridecyl]-3-(2,3,4,5,6-pentafluorobenzyl)-2-oxetanone (trans diastereomers), the alcohol starting materials of Examples 74–77:
A 1st trans diastereomer, (3S,4S or 3R,4R)-4-[(R)-2-hydroxytridecyl]-3-(2,3,4,5,6-pentafluorobenzyl)-2-oxetanone, Rf value: 0.43, and
a 2nd trans diastereomer, (3R,4R or 3S,4S)-4-[(R)-2-hydroxytridecyl]-3-(2,3,4,5,6-pentafluorobenzyl)-2-oxetanone, Rf value: 0.39 (chromatography and thin-layer chromatography on silica gel with ethyl acetate/methylene chloride/n-hexane (1:4.5:4.5)).

EXAMPLE T a) A solution of 0.5 ml of diisopropylamine in 15 ml of THF was treated at 0° C. with 2.0 ml of a solution of 1.6M n-butyllithium in hexane and, after stirring, cooled to −75° C. Then, a solution of 765 mg of N-benzyl-N-phenylglycine methyl ester in 3 ml of THF was added. After stirring a solution of 700 mg of (R)-3-(t-butyldimethylsiloxy)tetradecanal (Example Bb)) in 5 ml of THF was added dropwise. After stirring at −75° C. the reaction mixture was poured into aqueous potassium hydrogen sulphate and extracted with ether. The ether phase was dried, concentrated, partitioned between hexane and methanol/water (7:3), the hexane phase was dried and concentrated and the residue was chromatographed on silica gel with pentane/ether (5:1). There were obtained 96.3 mg of methyl (5R)-2-(N-benzylanilino)-5-(t-butyldimethylsiloxy)-3-hydroxyhexadecanoate, diastereomer A, MS: 540 (M+–C$_4$H$_9$·), and 142.8 mg of methyl (5R)-2-(N-benzylanilino)-5-(t-butyldimethylsiloxy)-3-hydroxyhexadecanoate, diastereomer B, MS: 540 (M+–C$_4$H$_9$·), and 313.4 g of a mixture of the above two diastereomers.

b) 134 mg of diastereomer B were suspended in 3 ml of 0.1N NaOH and treated with sufficient acetonitrile to form a clear solution. After stirring the mixture was poured into aqueous potassium hydrogen sulphate and extracted with ether and the ether phase was dried and concentrated. After chromatography on silica gel with methylene chloride/methanol (9:1) there were obtained 108 mg of (5R)-2-(N-benzylanilino)-5-(t-butyldimethylsiloxy)-3-hydroxyhexadecanoic acid, diastereomer B, MS: 526 (M+–C$_4$H$_9$·).

c) Analogously, from diastereomer A from a) there was obtained (5R)-2-(N-benzylanilino)-5-(t-butyldimethylsiloxy)-3-hydroxy- hexadecanoic acid, diastereomer A, MS: 526 (M+–C$_4$H$_9$·).

d) 1.1 g of diastereomer B from b), 1.1 g of HBTU, 0.5 g of triethylamine and 2 g of molecular sieve 4Å are stirred in 50 ml of acetonitrile. After filtration and concentration the product was chromatographed on silica gel with methylene chloride. There were thus obtained 1.04 g of 3R,4R (or 3S,4S)-3-(N-benzylanillrio)-4-[(R)-2-(t-butyldimethylsiloxy)tridecyl]-2-oxetanone, diastereomer B, MS: 566 (M+H)+.

e) Analogously, from diastereomer A from c) there was obtained 3S,4S (or 3R,4R)-3-(N-benzylanilino)-4-[(R)-2-(t-butyldimethyl-siloxy)tridecyl]-2-oxetanone, diastereomer A, MS: 566 (M+H)+.

f) 1.0 g of diastereomer B from d) and 0.8 g of Pd/C (10%) were hydrogenated in 30 ml of THF. Thereupon, the mixture was filtered and concentrated. There were obtained 834 mg of 3R,4R (or 3S,4S)-3-anilino-4-[(R)-2-(t-butyldimethylsiloxy)tridecyl]-2-oxetanone, diastereomer B, MS: 475 (M+·).

g) Analogously, from diastereomer A from e) there was obtained 3S,4S (or 3R,4R)-3-anilino-4-[(R)-2-(t-butyldimethylsiloxy)tridecyl]-2-oxetanone, diastereomer A, MS: 475 (M+·)).

h) The products of f) and g) were converted individually analogously to Example Be) into 3R,4R (or 3S,4S)-3-anilino-4-[(R)-2-hydroxytridecyl]-2-oxetanone, diastereomer B, m.p. 104° C., and, respectively 3S,4S (or 3R,4R)-3-anilino-4-[(R)-2-hydroxytridecyl]-2-oxetanone, diastereomer A, m.p. 60°–62° C., the alcohol starting materials for Example 79.

The acids of the formula Q$^a$—OH are known or can be prepared in analogy to the known acids, for example by saponifying a corresponding lower alkyl ester in a solvent such as acetone or methanol with an alkali metal hydroxide such as potassium hydroxide in an alcohol such as ethanol or methanol. Thus, the acid starting materials of Examples 2d) and 2e) hereinafter were prepared as follows:

A solution of 3.8 g of ethyl 2-propylmalonamidate in 30 ml of acetone was treated with 22 ml of 1N KOH in ethanol and stirred for 4 hours, then concentrated, taken up in sodium bicarbonate solution and extracted with ethyl acetate. The aqueous phase was acidified to pH 2 at 0° C. with hydrochloric acid and extracted with ethyl acetate. The ethyl acetate phase was washed with brine, dried, concentrated and the residue was recrystallized from ethyl acetate/ether. There were obtained 1.96 g of 2-propylmalonic acid monoamide, m.p. 137° C.

The 2-phenethylmalonamic acid, m.p. 141.5° C., the acid starting material for Examples 58–59, was prepared analogously from ethyl 2-phenethylmalonamate.

The (+) and (−)-2-isopropylmalonic acid monoamide (the amide starting material of Example 11) was prepared as described hereinafter:

5.5 g of rac-2-isopropylmalonic acid monoamide and 12.0 g of quinidine were dissolved in 100 ml of boiling water, seeded with a few crystals of the quinidine salt of (S)-(+)-2-isopropylmalonic acid monoamide and then crystallized out. The crystallizate was filtered off under suction, washed with water and ether and dried; there were obtained 8.3 g of the quinidine salt of (S)-(+)-2-isopopylmalonic acid monoamide. This salt was dissolved in 10 percent hydrochloric acid and left at 5° C., the separated crystals were filtered off under suction, washed with water, dried and recrystallized again from water with the addition of a few drops of 1N hydrochloric acid. There were obtained 720 mg of (S)-(+)-2-isopropylmalonic acid monoamide, m.p. 174° C., $[\alpha]_{589}^{20} = +45.6°$ (ethanol, c=1).

The mother liquor resulting in the crystallization of the quinidine salt was made acid with 10% hydrochloric acid and left at 5° C., the separated crystals were filtered off under suction, washed with water, dried and again recrystallized from water with the addition of a few drops of 1N hydrochloric acid. There were obtained 850 mg of (R)-(−)-2-isopropylmalonic acid monoamide, m.p. 176° C., $[\alpha]_{589}^{20} = -45.6°$ (ethanol, c=1).

The acid starting material for Example 42 was prepared as follows:

a) 20.6 g of thiomorpholine were added dropwise to a solution of 13.6 g of methyl malonate monochloride in 100 ml of methylene chloride. After stirring the mixture was diluted with 200 ml of methylene chloride, washed with water in a separating funnel, then dried, filtered and evaporated. The residue was purified by chromatography on silica gel with methylene chloride and then methylene chloride/acetone (1:1). There were obtained 17.6 g of methyl tetrahydro-b-oxo-4H-1,4-thiazine-4-propionate.

b) 85 ml of 1N potassium hydroxide solution were added dropwise to a solution of 17.3 g of the ester from a) in 170 ml of acetone. After stirring and filtering the mixture was evaporated and the residue was triturated in 200 ml of acetone and then filtered. The filter cake was washed with acetone and dried. An aqueous solution of the resulting potassium salt was chromato- graphed with water on a cation exchanger column. The eluate was concentrated to dryness and the residue was triturated with ether and filtered off. There were obtained 13 g of tetrahydro-b-oxo-4H-1,4-thiazine-4-propionic acid, m.p. 119°–120° C.

The acid starting material for Example 44 was prepared as follows:

a) 33 ml of 1N potassium hydroxide solution were added dropwise to a solution of 5.6 g of methyl 1-carbamoylcyclopentanecarboxylate in 66 ml of acetone. After stirring the mixture was treated with 250 ml of acetone and the separated potassium salt was filtered off and then washed with acetone and dried.

b) A solution of the 5.79 g of potassium salt obtained in 35 ml of water was acidified to pH1 with 4 ml of conc. hydrochloric acid at 0° C. The precipitate was filtered off and washed with water and then with diethyl ether. 3.5 g of 1-carbamoylcyclopentanecarboxylic acid were obtained after drying.

The acid starting material for Example 46 was prepared as follows:

A solution of 10.4 g of monomethyl methoxymalonate in 70 ml of methylene chloride was added dropwise at −10° C. to 26 ml of 25 percent aqueous ammonia. After stirring the mixture was evaporated and the residue was dissolved in water and chromato- graphed on a cation exchanger with water. The eluate was concentrated and the residue was triturated with diethyl ether and filtered off. The precipitate was washed with water and dried. There were obtained 8.9 g of methoxymalonamic acid, m.p. 128°–130° C.

The acid starting material for Example 49 was prepared as follows:

A solution of 1.79 g of carbamoylmethylthioacetic acid in 42 ml of water was treated with 3.71 g of monoperoxyphthalic acid magnesium salt hexahydrate. After stirring the mixture was filtered and the filtrate was concentrated and acidified with 2 ml of conc. hydrochloric acid. After filtration the filtrate was percolated over a cation exchanger, eluted with water and the eluate was evaporated to dryness. The residue was suspended in acetone and filtered off. It was washed with acetone and dried. There were obtained 1.65 g of rac-[(carbamoylmethyl)sulphinyl]acetic acid, m.p. 137°–138° C.

The lower alkyl esters corresponding to the acids of formula $Q^a$—OH are known or can be prepared in analogy to the known esters, for example as described hereinafter starting from the monoester of the formula H—$(X)_n$—COOR″, wherein R″ is lower-alkyl, via the dicarboxylic acid monoester of the formula HO-CO—$(X)_n$—COOR″. Thus, the starting acid of Example 2f) was prepared as follows:

a) 48 ml of a 1.6M n-butyllithium solution in hexane were added dropwise at −15° C. to 11 ml of diisopropylamine and 5 g of 4Å, molecular sieve in 75 ml of THF. After 15 minutes the reaction mixture was cooled to −78° C. and a solution of 9.5 g of ethyl 1,3-dioxolane-2-carboxylate in 50 ml of THF was added dropwise. After stirring for 20 minutes $CO_2$ was introduced at a temperature below −70° C. After saturation the mixture was stirred at −75° C. for 20 minutes and then warmed to room temperature. After volatization of the $CO_2$ gas the reaction mixture was concentrated, the residue was treated with saturated bicarbonate solution and ethyl acetate, the ethyl acetate phase was discarded, the aqueous phase was acidified to pH 2 with potassium hydrogen sulphate and extracted with ethyl acetate. The ethyl acetate phase was dried and concentrated.

b) 0.93 ml of isobutyl chloroformate in 5 ml of THF was added dropwise at 0° C. to a solution of 1.08 g of the product from a), 1.1 ml of triethylamine and 3 g of molecular sieve 4Å in 30 ml of THF. After stirring for 40 minutes ammonia gas was introduced for 10 minutes and the reaction mixture was subsequently stirred overnight. Thereupon, it was filtered, the filtrate was concentrated and the residue was chromatographed on silica gel with methylene chloride/methanol (95:5). There were obtained 420 mg of ethyl 2-carbamoyl-1,3-dioxolane-2-carboxylate, m.p. 99°–100° C.

c) A solution of 190 mg of the product from b) in 10 ml of methanol was treated with 1 ml of 2N KOH in methanol and stirred at room temperature for 90 minutes. Thereupon, a solution of 280 mg of potassium hydrogen sulphate in 1 ml of water was added, the reaction mixture was suction filtered and the filtrate was evaporated. There was obtained 2-carbamoyl-1,3-dioxolane-2-carboxylic acid.

2-Carbamoyl-m-dioxane-2-carboxylic acid (the acid starting material for Example 3m) was obtained analogously from ethyl m-dioxane-2-carboxylate.

The acids of the formula $(R^3,R^4)NCO(X)_n$—COOH in which X is a group $=CHN(R,R^o)$ can be prepared starting from the corresponding dicarboxylic acid monoester of the formula HOCO—X—COOR″ via a corresponding succinimide and the corresponding amide ester of the formula $H_2NCO$—X—COOR″, for example as described hereinafter for the acid starting material of Example 9.

a) 4.54 g of dicyclohexylcarbodiimide, 4.16 g of monoethyl acetamino-malonate and 2.53 g of N-hydroxysuccinimide were added to 54 ml of THF at 0° C. After stirring for 1 hour the mixture was left to warm to room temperature and was stirred overnight. Then, it was cooled to 0° C. and filtered. The filtrate was treated with 20 ml of 25% aqueous ammonia solution, left to stand at room temperature over the day and at 4° C. overnight. Then, the solution was evaporated and the residual aqueous solution was treated with sodium bicarbonate. The aqueous phase was separated, the organic phase was washed with saturated sodium chloride solution, then dried and concentrated. The residue was filtered in hexane containing ethyl acetate. The crystals obtained were washed with ether and then dried. There were obtained 1.2 g of [D,L]-N-acetyl-2-carbamoylglycine ether ester, m.p. 126°–128° C.

b) A solution of 5.8 ml of 1N potassium hydroxide was added dropwise to a suspension of 1.09 g of the amide ester from a) in 7 ml of acetone. After stirring for 3 hours the mixture was concentrated and the residue was dissolved in aqueous sodium bicarbonate solution. The solution was extracted with ethyl acetate, the aqueous phase was acidified to pH 3 with hydrochloric acid while cooling and then percolated over an ion exchanger. The eluate was concentrated to dryness and the residue was triturated with acetone. There were obtained 500 mg of [D,L]-N-acetyl-2-carbamoylglycine, m.p. 120° C. (decomposition).

Acid starting materials of the formula $(R^3,R^4)NCO(X)_n$—COOH in which at least one of $R^3$ and $R^4$ is different from H can be prepared by reacting the corresponding acid ester of the formula HOC(O)—(X)_n—C(O)O—R″ with an amine $HN(R^3,R^4)$.

Thus, the acid starting material of Example 10d was prepared as follows:

A solution of 3 g of monomethyl malonate in 15 ml of 40% aqueous dimethylamine was concentrated after stirring for 18 hours, filtered through a strongly acidic cation exchanger, concentrated to dryness and crystallized from chloroform. Concentration of the mother liquor and crystallization from ether yielded 1.3 g of dimethylcarbamoylacetic acid, m.p. 72°–76° C.

The compounds of formula I have valuable pharmacological properties. In particular, they inhibit pancreas lipase and can accordingly be used in the control or prevention of obesity, hyperlipemia, atherosclerosis and arteriosclerosis, in mammals, both human and non-human.

The inhibition of pancreas lipase by the oxetanones of formula I can be demonstrated experimentally by measuring titrimetrically the oleic acid liberated in the cleavage of triolein by hog pancreas lipase. To an emulsion which contains 1 mM of taurodeoxycholate, 9 mM of taurocholate, 0.1 mM of cholesterol, 1 mM of egg lecithin, 15 mg/ml of BSA, 2 mM of Tris HCl, 100 mM of sodium chloride, 1 mM of calcium chloride and triolein as the substrate was added the compound of formula I dissolved in ethanol or dimethyl sulphoxide (10% of the emulsion volume) and the reaction was started by the addition of 1–3 μg of hog pancreas lipase. The pH was held at 8 during the reaction by the addition of sodium hydroxide solution. The $IC_{50}$ was calculated from the consumption of sodium hydroxide solution determined during 10 minutes. The $IC_{50}$ is that concentration at which the lipase activity is inhibited to half of the maximum. The following Table contains the $IC_{50}$ values determined for the compounds of formula I.

| Example | 1a, 11a | 1b, 11b | 2b, 12b | 2d | 2e | 2f | 2g1, 13a | 2g2 | |
|---|---|---|---|---|---|---|---|---|---|
| $IC_{50}$ | 0.032 | 0.025 | 0.063 | 0.12 | 0.051 | 0.47 | 0.052 | 0.013 | |
| Example | 3c | 3d | 3e | 3f | 3g | 3h | 3i | 3j | |
| $IC_{50}$ | 0.39 | 0.90 | 1.41 | 0.083 | 0.294 | 2.1 | 0.42 | 0.16 | |
| Example | 3k | 3l | 14a | 6b, 14c | 7b | 10a | 10b | 10c | |
| $IC_{50}$ | 0.12 | 0.78 | 0.16 | 0.056 | 0.079 | 0.083 | 0.042 | 0.1 | |
| Example | 10d | 10e | 10f | 37 | 43 | 45 | 51 | 78c | 78d |
| $IC_{50}$ | 0.47 | 0.027 | 0.32 | 0.034 | 0.12 | 0.047 | 0.36 | 0.28 | 0.051 |

The acute toxicity (after single oral administration to mice) amounts to more than 5000 mg/kg for the products of Examples 3d, 3h, 3i, 3l, 4a and 10a, b, e and f.

The oxetanones of formula I can be used as medicaments, for example in the form of pharmaceutical preparations. The pharmaceutical preparations can be administered orally, for example in unit dosage forms such as tablets, coated tablets, dragees, hard and soft gelatine capsules, solutions, emulsions or suspensions.

For the manufacture of pharmaceutical preparations the products in accordance with the invention can be processed with pharmaceutically inert, inorganic or organic carriers. Lactose, maize starch or derivatives thereof, talc, stearic acid or its salts can be used, for example, as such carriers for tablets, coated tablets, dragees and hard gelatine capsules. Suitable carriers for soft gelatine capsules are, for example, vegetable oils, waxes, fats, semi-solid and liquid polyols; depending on the nature of the active ingredient no carriers are, however, generally required in the case of soft gelatine capsules. Suitable carriers for the manufacture of solutions and syrups are, for example, water, polyols, saccharose, invert sugar and glucose.

Moreover, the pharmaceutical preparations can contain preserving agents, solubilizers, stabilizing agents, wetting agents, emulsifying agents, sweetening agents, coloring agents, flavoring agents, salts for varying the osmotic pressure, buffers, coating agents or antioxidants. They can also contain still other therapeutically valuable substances.

As mentioned earlier, medicaments containing an oxetanone of formula I are likewise an object of the present invention, as is a process for the manufacture of such medicaments which comprises bringing an oxetanone of formula I and, if desired, one or more other therapeutically valuable substances into a galenical administration form. As mentioned, the compounds of formula I can be used in the control or prevention of illnesses, especially in the control or prevention of obesity, hyperlipemia, atherosclerosis and arteriosclerosis, in mammals, both human and non-human. The dosage can vary within wide limits and will, or course, be filled to the individual requirements in each particular case. In general, in the case of oral administration a daily dosage of about 0.1 mg to 100 mg/kg body weight should be appropriate.

The oxetanones of formula I can also be added to industrially-produced foodstuffs, whereby fats, oils, butter, margarine, chocolate and other confectionery goods especially come into consideration. Such industrially-produced foodstuffs, which can contain about 0.1 to 5 wt.% of an oxetanone of formula I, and their manufacture are likewise objects of the present invention.

The following Examples illustrate the present invention in more detail, but they are not intended to limit its scope in any manner. All temperatures are given in degrees Celsius.

EXAMPLE 1

A solution of 574 mg of (3S,4S)-3-ethyl-4-[(R)-2-hydroxynonadecyl]-2-oxetanone, 525 mg of triphenylphosphine, 290 mg of 2-isopropylmalonic acid monoamide and 2 g of molecular sieve (4Å) in 10 ml of THF were treated which stirring at 0° with 0.4 ml of diisopropyl azodicarboxylate. After stirring at 0° for 30 minutes and at room temperature (220 ° C.) for 1 hour the reaction mixture was filtered, the molecular sieve was washed with ether and the solvent was evaporated. The residue was dissolved in hexane and extracted with methanol/water (7:3). The hexane phase was diluted with ether, dried and evaporated. The residue was chromatographed on silica gel with methylene chloride/ether (9:1). There were obtained
 a) 239 mg of (S)-[[(2S,3S)-3-ethyl-4-oxo-2-oxetanyl]methyl]octadecyl (R or S)-2-isopropylmalonamate, m.p. 115°, and
 b) 266 mg of (S)-[[(2S,3S)-3-ethyl-4-oxo-2-oxetanyl]methyl]octadecyl (S or R)-2-isopropylmalonamate, m.p. 118°.

EXAMPLE 2

Analogously to Example 1, from (3S,4S)-3-hexyl-4-[(R)-2-hydroxytridecyl]-2-oxetanone and 2-isopropylmalonic acid monoamide there were obtained
 a) (S)-1-[[(2S,3S)-3-hexyl-4-oxo-2-oxetanyl]methyl]dodecyl (R or S)-2-isopropylmalonamate, m.p. 136°, and
 b) (S)-1-[[(2S,3S)-3-hexyl-4-oxo-2-oxetanyl]methyl]dodecyl (S or R)-2-isopropylmalonamate, m.p. 82°;
 c) from (3S,4S)-3-hexyl-4-[(R)-2-hydroxytridecyl]-2-oxetanone and isopropylidenemalonic acid monoamide there was obtained (S)-1-[[(2S,3S)-3-hexyl-4-oxo-2-oxetanyl]methyl]dodecyl 2-carbamoyl-3-methylcrotonate, m.p. 108°–111°;
 d) from (3S,4S)-3-hexyl-4-[(R)-2-hydroxytridecyl]-2-oxetanone and 2-propylmalonic acid monoamide there was obtained (S)-1-[[(2S,3S)-3-hexyl-4-oxo-2-oxetanyl]methyl]dodecyl-(RS)-2-carbamoylvalerate (epimers 1:1), m.p. 92°–94°;
 e) from (3S,4S)-3-ethyl-4-[(R)-2-hydroxynonadecyl]-2-oxetanone and 2-propylmalonic acid monoamide there was obtained (S)-1-[[(2S,3S)-3-ethyl-4-oxo-2-oxetanyl]methyl]octadecyl-(RS)-2-carbamoylvalerate (epimers 1:1), m.p. 78°–80°;
 f) from (3S,4S)-ethyl-4-[(R)-2-hydroxynonadecyl]-2-oxetanone and 2-carbamoyl-1,3-dioxolan-2-carboxylic acid there was obtained (S)-1-[[(2S,3S)-3-ethyl-4-oxo-2-oxetanyl]methyl]octadecyl-2-carbamoyl-1,3-dioxolane-2-carboxylate, m.p. 95°;
 g) from (3S,4S)-3-ethyl-4-[(R,10Z,13Z)-2-hydroxy-10,13-nonadecadienyl]-2-oxetanone and 2-isopropylmalonic acid monoamide there were obtained
  1. (all Z,S)-1-[[(2S,3S)-3-ethyl-4-oxo-2-oxetanyl]methyl]-9,12-octadecadienyl-(R or S)-2-isopropylmalonamate, m.p. 87°–88° (from ether) and
  2. (all Z,S)-1-[[(2S,3S)-3-ethyl-4-oxo-2-oxetanyl]methyl]-9,12-octadecadienyl-(S or R)-2-isopropylmalonamate, IR: 3393, 1840, 1716, 1647, 1185 cm$^{-1}$.

EXAMPLE 3

The following ester amides were obtained analogously to Example 1 by reacting (3S,4S)-3-hexyl-4-[(R)-2-hydroxytridecyl]-2-oxetanone with the following amides:
 a) with 4-carbamoylbutyric acid the 4-carbamoylbutyric acid (S)-1-[[(2S,3S)-3-hexyl-4-oxo-2-oxetanyl]methyl]dodecyl ester, m.p. 67°–68°,
 b) with 3-carbamoylpropionic acid the 3-carbamoylpropionic acid (S)-1-[[(2S,3S)-3-hexyl-4-oxo-2-oxetanyl]methyl]dodecyl ester, m.p. 50.5°–51°,
 c) with 2-carbamoylacetic acid the 2-carbamoylacetic acid (S)-1-[[(2S,3S)-3-hexyl-4-oxo-2-oxetanyl]methyl]dodecyl ester, m.p. 86.5°–87°,
 d) with oxalic acid monoamide the (S)-1-[[(2S,3S)-3-hexyl-4-oxo-2-oxetanyl]methyl]dodecyloxamate, m.p. 77°–78°,
 e) with methylcarbamoylacetic acid the (S)-1-[[(2S,3S)3-hexyl-4-oxo-2-oxetanyl]methyl]dodecyl-N-methylmalonamate, m.p. 63°–67°,
 f) with rac-2-carbamoyl-4-methylvaleric acid the (S)-1-[[(2S,3S) -3 -hexyl-4-oxo-2-oxetanyl]methyl]-dodecyl-(RS)-2-carbamoyl-4-methylvalerate (epimere 1:1), m.p. 102°–104°,
 g) with 1-carbamoylcyclohexanecarboxylic acid the (S)-1-[[(2S,3S)-3-hexyl-4-oxo-2-oxetanyl]methyl]-dodecyl-1-carbamoylcyclohexanecarboxylate, m.p. 50°–52°,
 h) with 2,2-dimethylmalonamidic acid the (S)-1-[[(2S,3S)3-hexyl-4-oxo-2-oxetanyl]methyl]dodecyl-2,2-dimethylmalonamate, $[\alpha]_D^{20}= -23.8°$ (CHCl$_3$, c=0.9%),
 i) with rac-2-methylmalonamidic acid the (S)-1-[[(2S,3S)3-hexyl-4-oxo-2-oxetanyl]methyl]dodecyl-(RS)-2-methylmalonamate (epimers 1:1), m.p. 107°–108°, j) with rac-2-ethylmalonamidic acid the (S)-1-[[(2S,3S)3-hexyl-4-oxo-2-oxetanyl]methyl]dodecyl-(RS)-2-ethylmalonamate (epimers 1:1), m.p. 87°–90°, k) with rac-2-butylmalonamidic acid the (S)-1-[[(2S,3S)-3-hexyl-4-oxo-2-oxetanyl]methyl]dodecyl-(RS)-2-butylmalonamate (epimers 1:1), m.p. 96°–98°, l) with 2,2-diethylmalonamidic acid the (S)-1-[[(2S,3S)-3-hexyl-4-oxo-2-oxetanyl]methyl]dodecyl-2,2-diethylmalonamate, $[\alpha]_D^{20} = -21.1°$ (CHCl$_3$, c=1%), m) with 2-carbamoyl-m-dioxane-2-carboxylic acid the (S)-1-[[(2S,3S)-3-hexyl-4-oxo-2-oxetanyl]methyl]dodecyl-2-carbamoyl-m-dioxane-2-carboxylate, m.p. 51°.

EXAMPLE 4

Analogously to Example 1, from (3S,4S)-3-ethyl4-[(R)-2-hydroxynonadecyl]-2-oxetanone and a) 1-carbamoylcyclohexanecarboxylic acid there was obtained (S)-1-[[(2S,3S)-3-ethyl-4-oxo-2-oxetanyl]methyl]octadecyl-1-carbamoylcyclohexanecarboxylate, m.p. 78°–79°, and b) 2-carbamoyl-m-dioxane-2-carboxylic acid there was obtained (S)-1-[[(2S,3S)-3-ethyl-4-oxo-2-oxetanyl]methyl]octadecyl-2-carbamoyl-m-dioxane-2-carboxylate, m.p. 79°.

EXAMPLE 5

Analogously to Example 1, from (3R,4R or 3S,4S)-4[(R)-2-hydroxytridecyl]-3-pentylthio-2-oxetanone and 2-isopropylmalonic acid amide there were obtained a) (S)-1-[[(2R,3R or 2S,3S)-4-oxo-3-pentylthio2-oxetanyl]methyl]dodecyl-(R or S)-2-isopropylmalonamate, MS: 354 [M+–(2-isopropylmalonic acid amide)]; IR (cm$^{-1}$): 3397, 2924, 1829, 1731, 1657, 1120, and b) (S)-1-[[(2R,3R or 2S,3S)-4-oxo-3-pentylthio2-oxetanyl]methyl]dodecyl-(S or R)-2-isopropylmalonamate, m.p. 77°–78° (diethyl ether).

EXAMPLE 6

Analogously to Example 1, from (3S,4S or 3R,4R)-4[(R)-2-hydroxytridecyl]-3-pentylthio-2-oxetanone and 2-isopropylmalonic acid amide there were obtained a) (S)-1-[[(2S,3S or 2R,3R)-4-oxo-3-pentylthio-2-oxetanyl]methyl]dodecyl-(R or S)-2-isopropylmalonamate, m.p. 133° (ethyl acetate), and b) (S)-1-[[(2S,3S or 2R ,3R)-4-oxo-3-pentylthio-2-oxetanyl]methyl]dodecyl-[S:R or R:S(2:1)]-2-isopropylmalonamate, m.p. 102°–104° (ethyl acetate).

EXAMPLE 7

Analogously to Example 1, from 3-benzyl-4-[(R)-2-hydroxytridecyl]-2-oxetanone and 2-isopropylmalonic acid monoamide there was obtained an epimer mixture which was separated by chromatography on silica gel with ethyl acetate/hexane/methylene chloride (1:2:2) into a) (S)-1-[[(2R,3R)-3-benzyl-4-oxo-2-oxetanyl]methyl]dodecyl-(R or S)-2-isopropylmalonamate, m.p. 85°–87° (methylene chloride), and b) (S)-1-[[(2R ,3R)-3-benzyl-4-oxo-2-oxetanyl]methyl]dodecyl-(S or R)-2-isopropylmalonamate, m.p. 108°–110° (methylene chloride).

EXAMPLE 8

Analogously to Example 1, from 3-benzyl-4-[(R)-2-hydroxytridecyl]-2-oxetanone and 2-isopropylmalonic acid monoamide there was obtained an epimer mixture which was separated by chromatography on silica gel with ethyl acetate/hexane/methylene chloride (1:2:2) into a) (S)-1-[[(2S,3S)-3-benzyl-4-oxo-2-oxetanyl]methyl]-dodecyl-(R or S)-2-isopropylmalonamate, m.p. 107°–108° (methylene chloride), and b) (S)-1-[[(2S,3S)-3-benzyl-4-oxo-2-oxetanyl]methyl]-dodecyl-(S or R)-2-isopropylmalonamate, m.p. 148°–149° (methylene chloride).

EXAMPLE 9

1.03 g of di-t-butyl azodicarboxylate were added to a suspension, cooled to −10° C., of 1.06g of (3S,4S)-3-hexyl-4-[(R)-2-hydroxytridecyl]-2-oxetanone, 480 mg of [D,L]-N-acetyl-2-carbamoylglycine, 1.1 g of triphenylphosphine and 1.2g of molecular sieve 4Å in 12 ml of THF. After stirring at 0° C. for 1 hour and at room temperature (20°C.) overnight the reaction mixture was worked-up analogously to that described in Example 1. There were obtained a) 190 mg of (S)-1-[[(2S,3S)-3-hexyl-4-oxo-2-oxetanyl]methyl]dodecyl-(R or S)-2-acetamidomalonamate, m.p. 125°–126°, and b) 100 mg of (S)-1-[[(2S,3S)-3-hexyl-4-oxo-2-oxetanyl]methyl]dodecyl-(R or S)-2-acetamiclomalonamate (epimers 1:1), m.p. 110°–116°, $[\alpha]_D^{25} = -8°$ (c=0.5, CHCl$_3$)

EXAMPLE 10

The following ester amides were obtained analogously to Example 1, but using the following amides:

a) from oxalic acid monoamide the (S)-1-[[(2S,3S)-3-ethyl-4-oxo-2-oxetanyl]methyl]octadecyl oxamate, m.p. 99°–100°, b) from 2-carbamoylacetic acid the (S)-1-[[(2S,3S)-3-ethyl-4-oxo-2-oxetanyl]methyl]octadecyl malonamate, m.p. 90.5°–91.5°, c) from methylcarbamoylacetic acid the (S)-1-[[(2S,3S)-3-ethyl-4-oxo-2-oxetanyl]methyl]octadecyl-N-methylmalonamate, m.p. 84°–85°, d) from dimethylcarbamoylacetic acid the (S)-1-[[(2S,3S)-3-ethyl-4-oxo-2-oxetanyl]methyl]octadecyl-N,N-dimethylmalonareate, m.p. 66°–67°, e) from rac-2-ethylmalonamidic acid (S)-1-[[(2S,3S-3-ethyl-4-oxo-2-oxetanyl]methyl]octadecyl-(RS)-2-methylmalonamate (epimers 1:1), m.p. 91.5°–92°, f) from 3-carbamoylpropionic acid the (S)-1-[[(2S,3S)3-ethyl-4-oxo-2-oxetanyl]methyl]octadecylsuccinamate, m.p. 74.5°–75.7°.

EXAMPLE 11

Analogously to Example 1, but using (S)-(+)- or (±)-2-isopropylmalonic acid monoamide, there were obtained a) (S)-[[(2S,3S)-3-ethyl-4-oxo-2-oxetanyl]methyl]octadecyl-(R)-2-isopropylmalonamate, m.p. 115°, and b) (S)-[[(2S,3S)-3-ethyl-4-oxo-2-oxetanyl]methyl]octadecyl-(S)-2-isopropylmalonamate, m.p. 118°.

EXAMPLE 12

Analogously to Examples 1, 2a), 2b) and 11, from (3S,4S)-3-hexyl-4-[(R)-2-hydroxytridecyl]-2-oxetanone and (±)- and (S)-(+)-2-isopropylmalonic acid monoamide there were obtained
  a) (S)-1-[[(2S,3S)-3-hexyl-4-oxo-2-oxetanyl]methyl]-dodecyl-(R)-2-isopropylmalonamate, m.p. 136°, and respectively,
  b) (S)-1-[[(2S,3S)-3-hexyl-4-oxo-2-oxetanyl]methyl]-dodecyl-(S)-2-isopropylmalonamate, m.p. 82°,
  c) from (3S,4S)-3-hexyl-4-[(R)-2-hydroxytridecyl]-2-oxetanone and 2-propylmalonic acid monoamide, after separation by chromatography on silica gel with methylene chloride/acetonitrile (85:15),
     1. (S)-1-[[(2S,3S)-3-hexyl-4-oxo-2-oxetanyl]methyl]dodecyl-(R or S)-2-carbamoylvalerate, m.p. 113° (from methanol/water), and
     2. (S)-1-[[(2S,3S)-3-hexyl-4-oxo-2-oxetanyl]methyl]dodecyl-(S or R)-2-carbamoylvalerate, m.p. 85°.

EXAMPLE 13

Analogously to Examples 1, 2g) and 11, from (3S,4S)-3-ethyl-4-[(R,10Z,13Z)-2-hydroxy-10,13-nonadecadienyl]-2-oxetanone and (±)- and (S)-(+)-2-isopropylmalonic acid monoamide there were obtained
  a) (all Z,S)-1-[[(2S,3S)-3-ethyl-4-oxo-2-oxetanyl]methyl]-9,12-octadecadienyl-(R)-2-isopropylmalonamate, m.p. 87°–88° (from ether), and
  b) (all Z,S)-1-[[(2S,3S)-3-ethyl-4-oxo-2-oxetanyl]methyl]-9,12-octadecadienyl-(S)-2-isopropylmalonamate, m.p. 109° (from aqueous methanol).

EXAMPLE 14

Analogously to Examples 1, 6 and 11, from (3S,4S or 3R,4R)-4-[(R)-2-hydroxytridecyl]-3-pentylthio-2-oxetanone and (±)- and (S)-(+)-2-isopropylmalonamide there were obtained
  a) (S)-1-[[(2S,3S or 2R,3R)-4-oxo-3-pentylthio-2-oxetanyl]methyl]dodecyl-(R)-2-isopropylmalonamate, m.p. 133° (ethyl acetate),
  b) (S)-1-[[(2S,3S or 2R,3R)-4-oxo-3-pentylthio-2-oxetanyl]methyl]dodecyl-(S)-2-isopropylmalonamate, m.p. 93° (diethyl ether/hexane) and
  c) (S)-1-[[(2S,3S or 2R,3R)-4-oxo-3-pentylthio-2-oxetanyl]methyl]dodecyl-[S:R (2:1)]-2-isopropylmalonamate, m.p. 102°–104° (ethyl acetate).

EXAMPLE 15

Analogously to Examples 1 and 11, from (3S,4S or 3R,4R)-benzyl-4-[(R)-2-hydroxytridecyl]-2-oxo-3-oxetanecarbamate and (S)-(+)-2-isopropylmalonic acid monoamide there was obtained (S)-1-[[(2S,3S or 2R,3R)-3-[1-(benzyloxy)formamido]-4-oxo-2-oxetanyl]methyl]dodecyl-(S)-2-isopropylmalonamate, m.p. 133° (from ether/hexane).

EXAMPLE 16

Analogously to Examples 1 and 11,
  a) from (3R,4R)-4-[(R)-2-hydroxytridecyl]-3-(phenylthio)-2-oxetanone and (S)-(+)-2-Isopropylmalonic acid monoamide there was obtained (S)-1-[[(2R,3R)-4-oxo-3-(phenylthio)-2-oxetanyl]methyl]dodecyl-(S)-2-isopropylmalonamate, m.p. 88° (ether),
  b) from (3S,4S)-4-[(R)-2-hydroxytridecyl]-3-(phenylthio)-2-oxetanone and 2-isopropylmalonic acid monoamide there was obtained (S)-1-[[(2S,3S)-4-oxo-3-(phenylthio)-2-oxetanyl]methyl] dodecyl-(RS)-2-isopropylmalonamate (1:1 epimers), m.p. 109° (ether), and
  c) from (3R,4R)-4-[(R)-2-hydroxytridecyl]-3-(phenylthio)-2-oxetanone and 2-isopropylmalonic acid monoamide there were obtained the same products as in a) and (S)-1-[[(2R,3R)-4-oxo-3-(phenylthio)-2-oxetanyl]methyl]dodecyl-2-isopropylmalonamate (R:S=7:1), m.p. 85° (ether).

EXAMPLE 17

Analogously to Examples 1 and 11, from (S)-(+)-2-isopropylmalonic acid monoamide and the following alcohols there were obtained the following esters:
  a) From (3S,4S or 3R,4R)-4-[(R)-2-hydroxynonadecyl]-3-(methylthio)-2-oxetanone the (S)-1-[[(2S,3S or 2R,3R)-3-(methylthio)-4-oxo-2-oxetanyl]methyl]octadecyl-(S)-2-isopropylmalonamate, m.p. 133° (from ether),
  b) from (3R,4R or 3S,4S)-4-[(R)-2-hydroxynonadecyl]-3-(methylthio)-2-oxetanone the (S)-1-[[(2R,3R or 2S,3S)-3-(methylthio)-4-oxo-2-oxetanyl]methyl]octadecyl-(S)-2-isopropylmalonamate, m.p. 103° (from ether),
  c) from (3S,4R or 3R,4S)-4-[(R)-2-hydroxynonadecyl]-3-(methylthio)-2-oxetanone the (S)-1-[[(2R,3S or 2S,3R)-3-(methylthio)-4-oxo-2-oxetanyl]methyl]octadecyl-(S)-2-isopropylmalonamate, m.p. 96° (from ether/hexane), and
  d) from (3R,4S or 3S,4R)-4-[(R)-2-hydroxynonadecyl]-3-(methylthio)-2-oxetanone the (S)-1-[[(2S,3R or 2R,3S)-3-(methylthio)-4-oxo-2-oxetanyl]methyl]octadecyl-(S)-2-isopropylmalonamate, m.p. 120° (from ether/hexane).

EXAMPLE 18

Analogusly to Examples 1 and 11, from (R)-(−)-2-isopropylmalonic acid monoamide and
  a) (3S,4S or 3R,4R)-4-[(R)-2-hydroxynonadecyl]-3-(methylthio)-2-oxetanone there was obtained (S)-1-[[(2S,3S or 2R,3R)-3-(methylthio)-4-oxo-2-oxetanyl]methyl]octadecyl-(R)-2-isopropylmalonamate, m.p. 96° (from ether),
  b) (3R,4R or 3S,4S)-4-[(R)-2-hydroxynonadecyl]-3-(methylthio)-2-oxetanone there was obtained (S)-1-[[(2R,3R or 2S,3S)-3-(methylthio)-4-oxo-2-oxetanyl]methyl]octadecyl-(R)-2-isopropylmalonamate, m.p. 87° (from ether/hexane).

EXAMPLE 19

In analogy to Examples 1 and 11, from (S)-(+)-2-isopropylmalonic acid monoamide and the following alcohols there were obtained the following esters:
  a) From (3S,4S or 3R,4R)-3-(benzylthio)-4-[(R)-2-hydroxytridecyl]-2-oxetanone the (S)-1-[[(2S,3S or 2R,3R)-3-(benzylthio)-4-oxo-2-oxetanyl]methyl]dodecyl-(S)-2-isopropylmalonamate, m.p. 84° (from pentane),
  b) from (3R,4R or 3S,4S)-3-(benzylthio)-4-[(R)-2-hydroxytridecyl]-2-oxetanone the (S)-1-[[(2R,3R or 2S,3S)-3-(benzylthio)-4-oxo-2-oxetanyl]methyl]dodecyl-(S)-2-isopropylmalonamate, m.p. 65° (from ether/pentane) and
  c) from (3S,4R and 3R,4S)-3-(benzylthio)-4-[(R)-2-hydroxytridecyl]-2-oxetanone
     1. the (S)-1-[[(2S,3R or 2R,3S)-3-(benzylthio)-4-oxo-2-oxetanyl]methyl]dodecyl-(S)-2-isopropylmalonamate, m.p. 69° (from pentane), and
     2. the (S)-1-[[(2R,3S or 2S,3R)-3-(benzylthio)-4-oxo-2-oxetanyl]methyl]dodecyl-(S)-2-isopropylmalonamate, m.p. 106° (from hexane).

EXAMPLE 20

In analogy to Examples 1 and 11, from (R)-(—)-2-isopropylmalonic acid monoamide and the following alcohols there were obtained the following esters:

a) From (3S,4S or 3R,4R)-3-(benzylthio)-4-[(R)-2-hydroxytridecyl]-2-oxetanone the (S)-1-[[(2S,3S or 2R,3R)-3-(benzylthio)-4-oxo-2-oxetanyl]methyl]-dodecyl-(R)-2-isopropylmalonamate, m.p. 130° (from ether/pentane), b) from (3R,4R or 3S,4S)-3-(Benzylthio)-4-[(R)-2-hydroxytridecyl]-2-oxetanone the (S)-1-[[(2R,3R or 2S,3S)-3-(benzylthio) 4-oxo-2-oxetanyl]methyl]dodecyl-(R)-2-isopropylmalonamate, m.p. 119° (from hexan/pentane), and c) from (3S,4R and 3R,4S)-3-(benzylthio)-4-[(R)-2-hydroxytridecyl]-2-oxetanone
  1. the (S)-1-[[(2S,3R or 2R,3S)-3-(benzylthio)-4-oxo-2-oxetanyl]methyl]dodecyl-(R)-2-isopropylmalonamate, m.p. 132° (from ether/pentane), and
  2. the (S)-1-[[(2R,3S or 2S,3R)-3-(benzylthio)-4-oxo-2-oxetanyl]methyl]dodecyl-(R)-2-isopropylmalonamate, m.p. 102° (from ether/pentane).

EXAMPLE 21

Analogously to Examples 1 and 11, by reacting (3R,4R)-3-ethyl-4-[(R)-2-hydroxynonadecyl]-2-oxetanone a) with (S)-(+)-2-Isopropylmalonic acid monoamide there was obtained (S)-1-[[(2R,3R)-3-ethyl-4-oxo-2oxetanyl]methyl]-octadecyl-(S)-2-isopropytmalonamate, m.p. 116°-118° (methylene chloride), and b) with 1-carbamoylcyclohexanecarboxylic acid there was obtained (S)-1-[[(2R,3R)-3-ethyl-4-oxo-2-oxetanyl]methyl]octadecyl-1-carbamoylcyclohexanecarboxylate, m.p. 71°-74°.

EXAMPLE 22

In analogy to Examples 1 and 11, a) from (S)-(+)-2-isopropylmalonic acid monoamide and (3R,4R)-4-[(R)-2-hydroxynonaclecyl]-3-methyl-2-oxetanone there was obtained (S)-1-[[(2R,3R)-3-methyl-4-oxo-2-oxetanyl]methyl]-octadecyl-(S)-2-isopropylmalonamate, m.p. 124°-126° (from ethyl acetate/hexane), and b) from rac-2-t-butylmalonic acid monoamide and (3R,4R)-4-[(R)-2-hydroxynonadecyl]-3-methyl-2-oxetanone there was obtained (S)-1-[[(2R,3R)-3-methyl-4-oxo-2-oxetanyl]methyl]-octadecyl-(RS)-2-t-butylmalonamate (epimers 1:1), m.p. 51°-54° (ethyl acetate/hexane).

EXAMPLE 23

A solution of 277 mg of (2S,3S,5S)-5-[[(cis)-2-carbamoylcyclohexyl]oxy]-2-hexyl-3-hydroxyhexadecanoic acid (Example Jd))in w4 ml of methylene chloride and 3 ml of DMF was treated with 2 g of molecular sieve (4Å), 240 mg of HBTU and 240 mg of triethylamine. After stirring 300 mg of HBTU and 300 mg of triethylamine were added thereto. The mixture was then filtered and the filtrate was concentrated. The residue was partitioned between methanol/water (7:3) and hexane and extracted with hexane. The hexane phase was diluted with methylene chloride, then dried and concentrated and the residue was recrystallized from ether/hexane. There were obtained a) 96 mg of (1R or S,2S or R)-2-[[(S)-1-[[(2S,3S)-3-hexyl-4-oxo-2-oxetanyl]methyl]dodecyl]oxy]cyclohexanecarboxamide (1 st cis diastereomer), m.p. 102° (from ether/hexane), and b) analogously from (2S,3S,5S)-5-[[(cis)-2-carbamoylcyclohexyl]oxy]-2-hexyl-3-hydroxyhexadecanoic acid (2nd diast. acid) in Example Je) there was obtained (1S or R,2R or S)-2-[[(S)-1-[[(2S,3S)-3-hexyl-4-oxo-2-oxetanyl]methyl]dodecyl]oxy]-cyclohexanecarboxamide (2nd cis diastereomer), m.p. 94° (from ether/hexane).

EXAMPLE 24

A solution of 42.5 mg of (2S,3S,5S)-5-[(R/S)-2-carbamoyl-1-methoxyethoxy]-2-hexyl-3-hydroxydecanoic acid (Example Kd)) in 10 ml of methylene chloride/acetonitrile (1:1) was treated with 1g of molecular sieve (4Å), 0.1 ml of triethylamine and 50 mg of HBTU. After stirring the reaction mixture was filtered and concentrated and the residue was partitioned between hexane and methanol/water (1:1); the aqueous methanolic phase was extracted with hexane, the hexane phase was dried and concentrated; the residue was subsequently chromatographed on silica gel with 5 percent methanol in methylene chloride. There were obtained 21 mg of (R/S)-3-[[(S)-1-[[(2S,3S)-3-hexyl-4-oxo-2-oxetanyl]methyl]dodecyl]oxy]-3-methoxypropionamide (epimers 3:1), m.p. 54°.

EXAMPLE 25

Ammonia gas was blown into a solution of 40 mg of 3-[[(S)-1-[[(2S,3S)-3-hexyl-4-oxo-2-oxetanyl]methyl]-dodecyl]oxy]propionic acid (Example L) in 2.5 ml of acetonitrile until the solution is saturated and subsequently 50 mg of HBTU were added. Then, the mixture was filtered and evaporated and the residue was chromato- graphed on silica gel with 5 percent methanol in methylene chloride. There were obtained 32.5 mg of (3S,4S)-4-[(S)-2-(2-carbamoylethoxy)tridecyl]-3-hexyl-2-oxetanone, m.p. 35°.

EXAMPLE 26

A solution of 33.5 mg of (S)-1-[[(2S,3S)-3-hexyl-4-oxo-2-oxetanyl]methyl]dodecyl hydrogen malonate (Example N) in 2 ml of acetonitrile was treated with 60 mg of HBTU and 75 mg of iso- propylamine. After stirring the reaction mixture was filtered, the filtrate was concentrated and the residue was chromatographed on silica gel with hexane/methylene chloride-/ethyl acetate (2:2:1). There were obtained 31.1 mg of (S)-1-[[(2S,3S)-3-hexyl-4-oxo-2-oxetanyl]methyl]dodecyl-N-isopropylmalonamate, m.p. 59°.

The following compounds were manufactured in an analogous manner to Example 1:

Example 27: (S)-1-[[(2S,3S)-3-Hexyl-4-oxo-2-oxetanyl]methyl]dodecyl-5-carbamoylvalerate, m.p. 50°-51°.

Example 28: (S)-1-[[(2S,3S)-3-Hexyl-4-oxo-2-oxetanyl]methyl]dodecyl -6-carbamoylhexanoate, m.p. 52°-53°, Example 29: (S)-1-[[(2S,3S)-3-Hexyl-4-oxo-2-oxetanyl]methyl]dodecyl-7-carbamoylheptanoate, m.p. 40°-43°, Example 30: (S)-1-[[(2S,3S)-3-Hexyl-4-oxo-2-oxetanyl]methyl]dodecyl-9-carbamoylnonanoate, m.p. 29°-30°, Example 31: (S)-1-[[(2S,3S)-3-Ethyl-4-oxo-2-oxetanyl]methyl]octadecyl-4-carbamoylbutyrate, m.p. 74°-75°, Example 32: (S)-1-[(2S,3S)-3-Ethyl-4-oxo-2-oxetanyl]methyl]octadecyl-adipamate, m.p. 63.5°-64.5°, Example 33: (S)-1-[[(2S,3S)-3-Ethyl-4-oxo-2-oxetanyl]methyl]octadecyl-6-carbamoylhexanoate, m.p. 71.5°-72.5°, Example 34: (S)-1-[[(2S,3S)-3-Hexyl-4-oxo-oxetanyl]methyl]dodecyl-(R or S)-2-t-butylmalonamate, m.p. 53°-54°, Example 35: (S)-1-[[(2S,3S)-3-Hexyl-4-oxo-2-oxetanyl]methyl]dodecyl-(S or R)-2-t-butylmalonamate, $[\alpha]_D^{20} = -16.4°$ (C=0.8, CHCl$_3$), Example 36: (S)-1-[[(2S,3S)-3-Ethyl-4-oxo-2-oxetanyl]methyl]octadecyl-(R or S)-2-t-butylmalonamate, m.p. 48°-49°, Example 37: (S)-1-[[(2S,3S)-3-Ethyl-4-oxo-2-oxetanyl]methyl]octadecyl-(S or R)-2-t-butylmalonamate, m.p. 81°-82°, Example 38: (S)-1-[[(2S,3S)-3-Hexyl-4-oxo-2-oxetanyl]methyl]dodecyl-(S)-3-[1-(benzyloxy)formamido]succinamate, m.p. 72°-73°, Example 39: (S)-1-[[(2S,3S)-3-Hexyl-4-oxo-2-oxetanyl]methyl]dodecyl-cis-6-carbamoyl-3-cyclohexene-1-carboxylate, m.p. 55°-59°, Example 40: (S)-1-[[(2S,3S)-3-Hexyl-4-oxo-2-oxetanyl]methyl]dodecyl-cis-2-carbamoylcyclohexanecarboxylate, m.p. 76°-77°, Example 41: (S)-1-[[(2S,3S)-3-Hexyl-4-oxo-2-oxetanyl]methyl]dodecyl-b-oxo-4-morphotinopropionate, m.p. 49°-51°, Example 42: (S)-1-[[(2S,3S)-3-Hexyl-4-oxo-2-oxetanyl]methyl]dodecyl-tetrahydro-b-oxo-4H-1,4-thiazine-4-propionate, m.p. 59°-61°, Example 43: (S)-1-[[(2S,3S)-3-Ethyl-4-oxo-2-oxetanyl]methyl]octadecyl-1-carbamoylcyclopentanecarboxylate, m.p. 62°-63°, Example 44: (S)-1-[[(2S,2S)-3-Hexyl-4-oxo-2-oxetanyl]methyl]dodecyl-1-carbamoylcyclopentanecarboxylate, m.p. 40°-41°, Example 45: (S)-1-[[(2S,3S)-3-Hexyl-4-oxo-2-oxetanyl]methyl]dodecyl-(RS)-2-benzylmatonomate (epimers 1:1), m.p. 86°-92°, Example 46: (S)-1-[[(2S,3S)-3-Hexyl-4-oxo-2-oxetanyl]methyl]dodecyl-(RS)-2-methoxymalonamate (epimers 1:1), m.p. 65°-67°, Example 47: (S)-1-[[(2S,3S)-3-Hexyl-4-oxo-2-oxetanyl]methyl]dodecyl-[(carbamoyl)thio]acetate, m.p. 58°-60°, Example 48: (S)-1-[[(2S,3S)-3-Aethyl-4-oxo-2-oxetanyl]methyl]octadecyl-[(carbamoylmethyl)thio]acetate, m.p. 83°-84° C., Example 49: (S)-1-[[(2S,3S)-3-Hexyl-4-oxo-2-oxetanyl]methyl]dodecyl-[(RS)-(carbamoylmethyl)sulphinyl]acetate (epimers 1:1), m.p. 55°-59°, Example 50: (S)-1-[[(2S,3S)-3-Ethyl-4-oxo-2-oxetanyl]methyl]octadecyl-[(RS)-(carbamoylmethyl)thio]acetate S-oxide, m.p. 80°-82°, Example 51: (S)-1-[[(2S,3S)-3-Hexyl-4-oxo-2-oxetanyl]methyl]dodecyl-3-[(2-carbamoylethyl)thio]propionate, m.p. 73°-74°, Example 52: (S)-1-[[(2S,3S)-3-Hexyl-4-oxo-2-oxetanyl]methyl]dodecyl-3-[(RS)-(2-carbamoylethyl)sulphinyl]propionate (epimers 1:1), m.p. 48°-51°, Example 53: (S)-1-[[(2S,3S)-3-Hexyl-4-oxo-2-oxetanyl]methyl]dodecyl-(carbamoylmethoxy)acetate, m.p. 52°-53°, Example 54: (S)-1-[[(2S,3S)-3-Ethyl-4-oxo-2-oxetanyl]methyl]octadecyl-(carbamoylmethoxy)acetate, m.p. 75°-76°, Example 55: (S)-1-[[(2S,3S)-3-Hexyl-4-oxo-2-oxetanyl]methyl]dodecyl-(RS)-2-[1-(benzyloxy)formamido]malonamate (epimers 1:1), m.p. 94°-95°, Example 56: (S)-1-[[(2S,3S)-3-Ethyl-4-oxo-2-oxetanyl]methyl]octadecyl-(RS)-2-isobutylmalonamate (epimers 1:1), m.p. 96°-99°, Example 57a): (S)-1-[[(2S,3S)-3-Ethyl-4-oxo-2-oxetanyl]methyl]octadecyl-(RS)-2-benzylmalonamate (epimers 1:1), m.p. 96°-103°, Example 57b): (S)-1-[[(2S,3S)-3-Ethyl-4-oxo-2-oxetanyl]methyl]octadecyl-(R or S)-2-benzylmalonamate, m.p. 118°-120°, Example 58: (S)-1-[[(2S,3S)-3-Hexyl-4-oxo-2-oxetanyl]methyl]dodecyl-(RS)-2-phenethylmalonamate (epimers 1:1), m.p. 92°-93°, Example 59: (S)-1-[[(2S,3S)-3-Ethyl-4-oxo-2-oxetanyl]methyl]octadecyl-(RS)-2-phenethylmalonamate (epimers 1:1), m.p. 97°-98°.

EXAMPLE 60

Analogously to Examples 1 and 11, from (S)-(+)-2-isopropylmalonic acid monoamide and (3R,4R)-4-[(R)-2-hydroxynonadecyl]-3-(2-propynyl)-2-oxetanone (Example M) there was obtained (S)-1-[[(2R,3R)-4-oxo-3-(2-propynyl)-2-oxetanyl]methyl]octadecyl-(S)-2-isopropylmalonamate, m.p. 92°-95° C. (from ethyl acetate/hexane).

EXAMPLE 61

Analogously to Examples 1 and 11, from (S)-(+)-2-isopropylmalonic acid monoamide and (3R,4R)-4-[(R)-2-hydroxynonadecyl]-3-propyl-2-oxetanone (Example O) there was obtained (S)-1-[[(2R,3R)-4-oxo-3-propyl-2-oxetanyl]methyl]-octadecyl-(S)-2-isopropylmalonamate, m.p. 90°-93° (from ethyl acetate/hexane).

The following compounds were manufactured in an analogous manner to Examples 1 and 11:

Example 62: (S)-1-[[(2S,3S)-3-(3-Methyl-2-butenyl)-4-oxo-2-oxetanyl]methyl]dodecyl-(R or S)-2-isopropylmalonamate, m.p. 100°-102°, Example 63: (S)-1-[[(2S,3S)-3-(3-Methyl-2-butenyl)-4-oxo-2-oxetanyl]methyl]dodecyl-(S or R)-2-isopropylmalonamate m.p. 120°-121°, Example 64: (S)-1-[[(2R,3R)-3-(3-Methyl-2-butenyl)-4-oxo-2-oxetanyl]methyl]dodecyl-(R or S)-2-isopropylmalonamate, m.p. 60°-62°, Example 65: (S)-1-[[(2R,3R)-3-(3-Methyl-2-butenyl)-4-oxo-2-oxetanyl]methyl]dodecyl-(S or R)-2-isopropylmalonamate m.p. 76°-78°, Example 66: (S)-1-[[(2S,3S or 2R,3R)-3-(5-Chloropentyl)-4-oxo-2-oxetanyl]methyl]dodecyl-(S)-2-isopropylmalonamate, m.p. 66°-72°, Example 67: (S)-1-[[(2S,3S or 2R,3R)-3-(5-Chloropentyl)-4-oxo-2-oxetanyl]methyl]dodecyl-(R)-2-isopropylmalonamate, m.p. 130°, Example 68: (S)-1-[[(2R,3R or 2S,3S)-3-(5-Chloropentyl)-4-oxo-2-oxetanyl]methyl]dodecyl-(S)-2-isopropylmalonamate, m.p. 44°-50°, Example 69: (S)-1-[[(2R,3R or 2S,3S)-3-(5-Chloropentyl)-4-oxo-2-oxetanyl]methyl]dodecyl-(R)-2-isopropylmalonamate, m.p. 85°-87°, Example 70: (S)-1-(2S,3S or 2R,3R)-[[3-[(E)-2-Butenyl]-4-oxo-2-oxetanyl]methyl]dodecyl-(R or S)-2-isopropylmalonamate, m.p. 105°–107°, Example 71: (S)-1-(2S,3S or 2R,3R)-[[3-[(E)-2-Butenyl]-4-oxo-2-oxetanyl]methyl]dodecyl-(S or R)-2-isopropylmalonamate, m.p. 96°–98°, Example 72: (S)-1-(2R,3R or 2S,3S)-[[3-[(E)-2-Butenyl]-4-oxo-2-oxetanyl]methyl]dodecyl-(S)-2-isopropylmalonamate, m.p. 89°–90°, Example 73: (S)-1-(2R,3R or 2S,3S)-[[3-[(E)-2-Butenyl]-4-oxo-2-oxetanyl]methyl]dodecyl-(R)-2-isopropylmalonamate, m.p. 60°–63°, Example 74: (S)-1-[[(2R,3R or 2S,3S)-3-(2,3,4,5,6-Pentafluorobenzyl)-2-oxetanyl]methyl]dodecyl-(R)-2-isopropylmalonamate, m.p. 107°–109°, Example 75: (S)-1-[[(2R,3R or 2S,3S)-3-(2,3,4,5,6-Pentafluorobenzyl)-2-oxetanyl]methyl]dodecyl-(S)-2-isopropylmalonamate, m.p. 115°–118°, Example 76: (S)-1-[[(2S,3S or 2R,3R)-3-(2,3,4,5,6-Pentafluorobenzyl)-2-oxetanyl]methyl]dodecyl-(R)-2-isopropylmalonamate, m.p. 88°–90°, and Example 77: (S)-1-[[(2S,3S or 2R,3R)-3-(2,3,4,5,6-Pentafluorobenzyl)-2-oxetanyl]methyl]dodecyl-(S)-2-isopropylmalonamate, m.p. 52°–55°.

EXAMPLE 78

Analogously to Examples 1 and 2, but using (R)- or (S)-2-pyrrolidone-5-carboxylic acid in place of 2-isopropylmalonic acid monoamide there were obtained
a) 5-oxo-D-proline-(S)-1-[[(2S,3S)-3-hexyl-4-oxo-2-oxetanyl]methyl]dodecyl ester, $^1$H-NMR (CDCl$_3$): 0.88 (m,6H); 1.26 (m,26H); 1.55–1.9 (m,4H); 1.95–2.55 (m,6H); 3.21 (m,1H); 4.25 (m,1H); 4.31 (m,1H); 5.14 (m,1H); 5.80 (s,1H) ppm,
b) 5-oxo-L-proline-(S)-1-[[(2S,3S)-3-hexyl-4-oxo-2-oxetanyl]methyl]dodecyl ester, m.p. 51°–52°,
c) 5-oxo-D-proline-(S)-1-[[(2S,3S)-3-ethyl-4-oxo-2-oxetanyl]methyl]octadecyl ester, m.p. 55° (diethyl ether), and
d) 5-oxo-L-proline-(S)-1-[[(2S,3S)-3-ethyl-4-oxo-2-oxetanyl]methyl]octadecyl ester, m.p. 57°–58°.

EXAMPLE 79

Analogously to Examples 1 and 11, from (S)-(+)-2-isopropylmalonic acid monoamide and
a) 3R,4R (or 3S,4S)-3-anilino-4-[(R)-2-hydroxytridecyl]-2-oxetanone, diastereomer B (Example T) there was obtained (S)-1-[[(2R,3R or 2S,3S)-3-anilino-4-oxo-2-oxetanyl]methyl]dodecyl-(S)-2-isopropylmalonamate (diastereomer B), m.p. 92°, and
b) from 3S,4S (or 3R,4R)-3-anilino-4-[(R)-2-hydroxytridecyl]-2-oxetanone, diastereomer A (Example T) there was obtained (S)-1-[[(2S,3S or 2R,3R)-3-anilino-4-oxo-2-oxetanyl)methyl]dodecyl-(S)-2-isopropylmalonamate (diastereomer A), m.p. 77°.

Pharmaceutical preparations of the following composition are manufactured in a manner known to those of ordinary skill in the art:

EXAMPLE AP

Soft gelatine capsules:

|  | Amount per capsule |
|---|---|
| An oxetanone of formula I | 50 mg |
| Medium-chain triglyceride | 450 ml |

EXAMPLE BP

Hard gelatin capsules:

| | |
|---|---|
| An oxetanone of formula I | 20.0 mg |
| Lactose cryst. | 37.0 mg |
| Microcrystalline cellulose | 20.0 mg |
| Polyvinylpyrrolidone | 8.5 mg |
| Sodium salt of the carboxymentyl ether of starch | 8.5 mg |
| Talc | 4.5 mg |
| Magnesium stearate | 1.5 mg |
| Capsule fill weight | 100.0 mg |

EXAMPLE CP

Tablets

| Tablets | |
|---|---|
| An oxetanone of formula I | 30.0 mg |
| Lactose anhydrous | 118.8 mg |
| Microcrystalline cellulose | 30.0 mg |
| Polyvinylpyrrolidone | 10.0 mg |
| Polymer of carboxymethylcellulose | 10.0 mg |
| Magnesium stearate | 1.2 mg |
| Tablet weight | 200.0 mg |

EXAMPLE DP

Tablets with controlled release of the active ingredient and increased residence time in the stomach:

| | |
|---|---|
| An oxetanone of formula I | 60.0 mg |
| Lactose powd. | 70.0 mg |
| Hydroxypropylmethylcellulose | 52.5 mg |
| Polyvinylpyrrolidone | 7.5 mg |
| Talc | 8.0 mg |
| Magnesium stearate | 1.0 mg |
| Colloidal silicic acid | 1.0 mg |
| Nucleus weight | 200.0 mg |
| Hydroxypropylmethylcellulose | 2.5 mg |
| Talc | 1.25 mg |
| Titanium dioxide | 1.25 mg |
| Weight of the film coating | 5.0 mg |

EXAMPLE EP

Reconstitutable powder:

| | |
|---|---|
| An oxetanone of formula I | 200.0 mg |
| Ethylvanillin | 10.0 mg |
| Aspartame (N-L-α-Aspartyl-L-phenylalanine-1-methyl ester) | 30.0 mg |
| Sprayed skinned milk powder | 4,760.0 mg |
| Total | 5,000.0 mg |

We claim:
1. A compound having the formula:

wherein R$^1$ and R$^2$ each are independently alkyl with up to 18C atoms substituted by 1 to 3 halogen atoms or alkyl, alkenyl, alkynyl or alkadienyl groups with up to 20C atoms optionally interrupted by a 1,4-arylene group, optionally substituted by an aryl group in the ω-position and optionally substituted by an aryl-$C_{1-4}$-alkyl group, whereby $R^1$ can be interrupted by an O or S atoms or by a sulphinyl or sulphonyl group in a position other than the α-position to an unsaturated C atom, or $R^1$ is an aryl—NH— or aryl-$C_{1-4}$-alkyl—OCONH— group, and $R^3$ is hydrogen or $C_{1-4}$-alkyl.

2. The compound of claim 1, wherein $R^3$ is hydrogen and $R^1$ and $R^2$ each are $C_{1-20}$-alkyl.

3. The compound of formula I according to claim 2 wherein $R^1$ and $R^2$ each are independently selected from the group consisting of hexyl and undecyl.

4. The compound 5-oxo-D-proline-(S)-1-[[(2S,3S)-3-ethyl-4-oxo-2-oxetanyl]methyl]octadecyl ester.

5. The compound 5-oxo-L-proline-(S)-1-[[(2S,3S)-3-ethyl-4-oxo-2-oxetanylmethyl]octadecyl ester.

6. A pharmaceutical composition which comprises a therapeutically effective amount of a compound having the formula

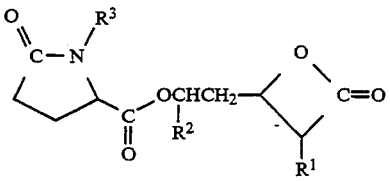

wherein $R^1$ and $R^2$ each are independently alkyl with up to 18C atoms substituted by 1 to 3 halogen atoms or alkyl, alkenyl, alkynyl or alkadienyl groups with up to 20C atoms optionally interrupted by a 1,4-arylene group, optionally substituted by an aryl group in the -ω position and optionally substituted by an aryl-$C_{1-4}$-alkyl group, whereby $R^1$ can be interrupted by an O or S atoms or by a sulphinyl or sulphonyl group in a position other than the α-position to an unsaturated C atom, or $R^1$ is an aryl—NH— or aryl-$C_{1-4}$-alkyl-OCONH — group, and $R^3$ is hydrogen or $C_{1-4}$-alkyl, and a therapeutically inert carrier.

7. The pharmaceutical compositions of claim 6 which is in unit dosage form.

8. The pharmaceutical composition of claim 7 wherein the amount of said compound is about 0.1 mg to about 100 mg.

9. The pharmaceutical composition of claim 7 wherein said unit dosage form is selected from the group consisting of soft gelatine capsules, solutions, emulsions, and suspensions.

* * * * *